United States Patent
Kim et al.

(10) Patent No.: US 9,241,763 B2
(45) Date of Patent: Jan. 26, 2016

(54) SYSTEMS, APPARATUS, METHODS AND PROCEDURES FOR THE NONINVASIVE TREATMENT OF TISSUE USING MICROWAVE ENERGY

(75) Inventors: Steven Kim, Los Altos, CA (US); Daniel Francis, Moutain View, CA (US); Jessi E. Johnson, Sunnyvale, CA (US); Alexey Salamini, San Francisco, CA (US); Ted Su, Sunnyvale, CA (US); Dong Hoon Chun, Sunnyvale, CA (US); Yoav Ben-Haim, San Francisco, CA (US)

(73) Assignee: MIRAMAR LABS, INC., Santa Clara, CA (US)

( * ) Notice: Subject to any disclaimer, the term of this patent is extended or adjusted under 35 U.S.C. 154(b) by 692 days.

(21) Appl. No.: 12/988,165

(22) PCT Filed: Apr. 17, 2009

(86) PCT No.: PCT/US2009/002403
§ 371 (c)(1),
(2), (4) Date: Oct. 15, 2010

(87) PCT Pub. No.: WO2009/128940
PCT Pub. Date: Oct. 22, 2009

(65) Prior Publication Data
US 2011/0040299 A1    Feb. 17, 2011

Related U.S. Application Data

(63) Continuation-in-part of application No. PCT/US2008/060922, filed on Apr. 18, 2008, and a continuation-in-part of application No. PCT/US2008/060940, filed on Apr. 18, 2008, and a
(Continued)

(51) Int. Cl.
*A61B 18/18* (2006.01)
*A61N 5/04* (2006.01)
(Continued)

(52) U.S. Cl.
CPC .............. *A61B 18/1815* (2013.01); *A61N 5/04* (2013.01); *A61B 2017/00106* (2013.01); *A61B 2018/00023* (2013.01); *A61B 2018/00291* (2013.01)

(58) Field of Classification Search
CPC ..................... A61B 18/18; A61B 2018/00023; A61B 18/14; A61B 18/1815; A61N 5/022; A61N 5/02; A61N 2005/007
USPC ........................................... 606/33; 607/101
See application file for complete search history.

(56) References Cited

U.S. PATENT DOCUMENTS

| 2,407,690 A | 9/1946 | Southworth |
| 3,307,553 A | 3/1967 | Liebner |

(Continued)

FOREIGN PATENT DOCUMENTS

| EP | 0139607 B1 | 4/1990 |
| EP | 0370890 B1 | 11/1995 |

(Continued)

OTHER PUBLICATIONS

Abraham et al.; Monopolar radiofrequency skin tightening; Facial Plast Surg Clin N Am; 15(2); pp. 169-177; May 2007.
(Continued)

*Primary Examiner* — Kaitlyn Smith
(74) *Attorney, Agent, or Firm* — Shay Glenn LLP

(57) ABSTRACT

The present invention is directed to systems, apparatus, methods and procedures for the noninvasive treatment of tissue, including treatment using microwave energy. In one embodiment of the invention a medical device and associated apparatus and procedures are used to treat dermatological conditions using, for example, microwave energy.

10 Claims, 24 Drawing Sheets

Related U.S. Application Data continuation-in-part of application No. PCT/US2008/060929, filed on Apr. 18, 2008, and a continuation-in-part of application No. PCT/US2008/060935, filed on Apr. 18, 2008, and a continuation-in-part of application No. 12/107,025, filed on Apr. 21, 2008, and a continuation-in-part of application No. PCT/US2008/013650, filed on Dec. 12, 2008.

(60) Provisional application No. 61/208,315, filed on Feb. 23, 2009, provisional application No. 61/196,948, filed on Oct. 22, 2008, provisional application No. 61/045,937, filed on Apr. 17, 2008, provisional application No. 60/912,899, filed on Apr. 19, 2007, provisional application No. 61/013,274, filed on Dec. 12, 2007.

(51) Int. Cl.
*A61B 17/00* (2006.01)
*A61B 18/00* (2006.01)

(56) References Cited

U.S. PATENT DOCUMENTS

| | | | |
|---|---|---|---|
| 3,527,227 | A | 9/1970 | Fritz |
| 3,693,623 | A | 9/1972 | Harte et al. |
| 3,845,267 | A | 10/1974 | Fitzmayer |
| 4,069,827 | A | 1/1978 | Dominy |
| 4,095,602 | A | 6/1978 | Leveen |
| 4,108,147 | A | 8/1978 | Kantor |
| 4,140,130 | A | 2/1979 | Storm, III |
| 4,174,713 | A | 11/1979 | Mehl |
| 4,190,053 | A | 2/1980 | Sterzer |
| 4,190,056 | A | 2/1980 | Tapper et al. |
| 4,197,860 | A | 4/1980 | Sterzer |
| 4,228,809 | A | 10/1980 | Paglione |
| 4,375,220 | A | 3/1983 | Matvias |
| 4,378,806 | A | 4/1983 | Henley Cohn |
| 4,388,924 | A | 6/1983 | Weissman et al. |
| 4,397,313 | A | 8/1983 | Vaguine |
| 4,397,314 | A | 8/1983 | Vaguine |
| 4,446,874 | A | 5/1984 | Vaguine |
| 4,528,991 | A | 7/1985 | Dittmar et al. |
| 4,589,424 | A | 5/1986 | Vaguine |
| 4,597,379 | A | 7/1986 | Kihn et al. |
| 4,614,191 | A | 9/1986 | Perler |
| 4,617,926 | A | 10/1986 | Sutton |
| 4,632,128 | A | 12/1986 | Paglione et al. |
| 4,641,649 | A | 2/1987 | Walinsky et al. |
| 4,669,475 | A | 6/1987 | Turner |
| 4,672,980 | A | 6/1987 | Turner |
| 4,690,156 | A | 9/1987 | Kikuchi et al. |
| 4,702,262 | A * | 10/1987 | Andersen et al. ............ 607/155 |
| 4,744,372 | A | 5/1988 | Kikuchi et al. |
| 4,747,416 | A | 5/1988 | Kikuchi et al. |
| 4,800,899 | A | 1/1989 | Elliott |
| 4,825,880 | A | 5/1989 | Stauffer et al. |
| 4,841,989 | A | 6/1989 | Kikuchi et al. |
| 4,841,990 | A | 6/1989 | Kikuchi et al. |
| 4,860,752 | A | 8/1989 | Turner |
| 4,881,543 | A | 11/1989 | Trembly et al. |
| 4,891,483 | A | 1/1990 | Kikuchi et al. |
| 4,945,912 | A | 8/1990 | Langberg |
| 4,974,587 | A | 12/1990 | Turner et al. |
| 5,059,192 | A | 10/1991 | Zaias |
| 5,097,846 | A | 3/1992 | Larsen |
| 5,101,836 | A | 4/1992 | Lee |
| 5,107,832 | A | 4/1992 | Guibert et al. |
| 5,143,063 | A | 9/1992 | Fellner |
| 5,186,181 | A | 2/1993 | Franconi et al. |
| 5,190,518 | A | 3/1993 | Takasu |
| 5,198,776 | A | 3/1993 | Carr |
| 5,226,907 | A | 7/1993 | Tankovich |
| 5,234,004 | A | 8/1993 | Hascoet et al. |
| 5,246,438 | A | 9/1993 | Langberg |
| 5,272,301 | A | 12/1993 | Finger et al. |
| 5,295,955 | A | 3/1994 | Rosen et al. |
| 5,301,692 | A | 4/1994 | Knowlton |
| 5,305,748 | A | 4/1994 | Wilk |
| 5,315,994 | A | 5/1994 | Guibert et al. |
| 5,316,000 | A | 5/1994 | Chapelon et al. |
| 5,364,336 | A | 11/1994 | Carr |
| 5,364,394 | A | 11/1994 | Mehl |
| 5,383,917 | A | 1/1995 | Desai et al. |
| 5,385,544 | A | 1/1995 | Edwards et al. |
| 5,405,346 | A | 4/1995 | Grundy et al. |
| 5,407,440 | A | 4/1995 | Zinreich et al. |
| 5,409,484 | A | 4/1995 | Erlich et al. |
| 5,421,819 | A | 6/1995 | Edwards et al. |
| 5,425,728 | A | 6/1995 | Tankovich |
| 5,431,650 | A | 7/1995 | Cosmescu |
| 5,433,740 | A | 7/1995 | Yamaguchi |
| 5,441,532 | A | 8/1995 | Fenn |
| 5,443,487 | A | 8/1995 | Guibert et al. |
| 5,462,521 | A | 10/1995 | Brucker et al. |
| 5,474,071 | A | 12/1995 | Chapelon et al. |
| 5,503,150 | A | 4/1996 | Evans |
| 5,507,741 | A | 4/1996 | L'Esperance, Jr. |
| 5,507,790 | A | 4/1996 | Weiss |
| 5,509,929 | A | 4/1996 | Hascoet et al. |
| 5,522,814 | A | 6/1996 | Bernaz |
| 5,531,662 | A | 7/1996 | Carr |
| 5,540,681 | A | 7/1996 | Strul et al. |
| 5,549,639 | A | 8/1996 | Ross |
| 5,553,612 | A | 9/1996 | Lundback |
| 5,569,237 | A | 10/1996 | Beckenstein |
| 5,571,154 | A | 11/1996 | Ren |
| 5,575,789 | A | 11/1996 | Bell et al. |
| 5,584,830 | A | 12/1996 | Ladd et al. |
| 5,586,981 | A | 12/1996 | Hu |
| 5,595,568 | A | 1/1997 | Anderson et al. |
| 5,649,973 | A | 7/1997 | Tierney et al. |
| 5,660,836 | A | 8/1997 | Knowlton |
| 5,662,110 | A | 9/1997 | Carr |
| 5,669,916 | A | 9/1997 | Anderson |
| 5,674,219 | A | 10/1997 | Monson et al. |
| 5,683,381 | A | 11/1997 | Carr et al. |
| 5,683,382 | A | 11/1997 | Lenihan et al. |
| 5,690,614 | A | 11/1997 | Carr et al. |
| 5,707,403 | A | 1/1998 | Grove et al. |
| 5,724,966 | A | 3/1998 | Lundback |
| 5,733,269 | A | 3/1998 | Fuisz |
| 5,735,844 | A | 4/1998 | Anderson et al. |
| 5,742,392 | A | 4/1998 | Anderson et al. |
| 5,743,899 | A | 4/1998 | Zinreich |
| 5,755,753 | A | 5/1998 | Knowlton |
| 5,769,879 | A | 6/1998 | Richards et al. |
| 5,776,127 | A | 7/1998 | Anderson et al. |
| 5,782,897 | A | 7/1998 | Carr |
| 5,810,801 | A | 9/1998 | Anderson et al. |
| 5,810,804 | A | 9/1998 | Gough et al. |
| 5,814,996 | A | 9/1998 | Winter |
| 5,824,023 | A | 10/1998 | Anderson |
| 5,830,208 | A | 11/1998 | Muller |
| 5,836,999 | A | 11/1998 | Eckhouse et al. |
| 5,868,732 | A | 2/1999 | Waldman et al. |
| 5,879,346 | A | 3/1999 | Waldman et al. |
| 5,891,094 | A | 4/1999 | Masterson et al. |
| 5,897,549 | A | 4/1999 | Tankovich |
| 5,902,263 | A | 5/1999 | Patterson et al. |
| 5,904,709 | A | 5/1999 | Arndt et al. |
| 5,919,218 | A | 7/1999 | Carr |
| 5,928,797 | A | 7/1999 | Vineberg |
| 5,931,860 | A | 8/1999 | Reid et al. |
| 5,949,845 | A * | 9/1999 | Sterzer ............................ 378/37 |
| 5,971,982 | A | 10/1999 | Betsill et al. |
| 5,979,454 | A | 11/1999 | Anvari et al. |
| 5,983,124 | A | 11/1999 | Carr |
| 5,983,900 | A | 11/1999 | Clement et al. |
| 5,989,245 | A | 11/1999 | Pescott |
| 6,015,404 | A | 1/2000 | Altshuler et al. |
| 6,024,095 | A | 2/2000 | Stanley, III |
| 6,026,331 | A | 2/2000 | Feldberg et al. |

(56) References Cited

U.S. PATENT DOCUMENTS

| | | | |
|---|---|---|---|
| 6,026,816 A | 2/2000 | McMillan et al. |
| 6,030,378 A | 2/2000 | Stewart |
| 6,036,632 A | 3/2000 | Whitmore, III et al. |
| 6,047,215 A | 4/2000 | McClure et al. |
| 6,050,990 A | 4/2000 | Tankovich et al. |
| 6,077,294 A | 6/2000 | Cho et al. |
| 6,080,146 A | 6/2000 | Altshuler et al. |
| 6,093,186 A | 7/2000 | Goble |
| 6,097,985 A | 8/2000 | Kasevich et al. |
| 6,104,959 A | 8/2000 | Spertell |
| 6,106,514 A | 8/2000 | O'Donnell, Jr. |
| 6,113,559 A | 9/2000 | Klopotek |
| 6,113,593 A | 9/2000 | Tu et al. |
| 6,126,636 A | 10/2000 | Naka |
| 6,129,696 A | 10/2000 | Sibalis |
| 6,139,569 A | 10/2000 | Ingle et al. |
| 6,149,644 A | 11/2000 | Xie |
| 6,162,212 A | 12/2000 | Kreindel et al. |
| 6,162,218 A | 12/2000 | Elbrecht et al. |
| 6,171,301 B1 | 1/2001 | Nelson et al. |
| 6,175,768 B1 | 1/2001 | Arndt et al. |
| 6,181,970 B1 | 1/2001 | Kasevich |
| 6,183,773 B1 | 2/2001 | Anderson |
| 6,187,001 B1 | 2/2001 | Azar et al. |
| 6,197,020 B1 | 3/2001 | O'Donnell, Jr. |
| 6,208,903 B1 | 3/2001 | Richards et al. |
| 6,210,367 B1 | 4/2001 | Carr |
| 6,214,034 B1 | 4/2001 | Azar |
| 6,223,076 B1 | 4/2001 | Tapper |
| 6,231,569 B1 | 5/2001 | Bek et al. |
| 6,235,016 B1 | 5/2001 | Stewart |
| 6,241,753 B1 | 6/2001 | Knowlton |
| 6,245,062 B1 | 6/2001 | Berube et al. |
| 6,264,652 B1 | 7/2001 | Eggers et al. |
| 6,273,884 B1 | 8/2001 | Altshuler et al. |
| 6,277,104 B1 | 8/2001 | Lasko et al. |
| 6,277,111 B1 | 8/2001 | Clement et al. |
| 6,277,116 B1 | 8/2001 | Utely et al. |
| 6,280,441 B1 | 8/2001 | Ryan |
| 6,283,956 B1 | 9/2001 | McDaniel |
| 6,283,987 B1 | 9/2001 | Laird et al. |
| 6,287,302 B1 | 9/2001 | Berube |
| 6,290,699 B1 | 9/2001 | Hall et al. |
| 6,293,941 B1 | 9/2001 | Strul et al. |
| 6,306,128 B1 | 10/2001 | Waldman et al. |
| 6,306,130 B1 | 10/2001 | Anderson et al. |
| 6,319,211 B1 | 11/2001 | Ito et al. |
| 6,322,584 B2 | 11/2001 | Ingle et al. |
| 6,325,769 B1 | 12/2001 | Klopotek |
| 6,330,479 B1 | 12/2001 | Stauffer |
| 6,334,074 B1 * | 12/2001 | Spertell | 607/101 |
| 6,347,251 B1 | 2/2002 | Deng |
| 6,350,263 B1 | 2/2002 | Wetzig et al. |
| 6,350,276 B1 | 2/2002 | Knowlton |
| 6,361,531 B1 | 3/2002 | Hissong |
| 6,364,876 B1 | 4/2002 | Erb et al. |
| 6,383,176 B1 | 5/2002 | Connors et al. |
| 6,387,103 B2 | 5/2002 | Shadduck |
| 6,402,739 B1 | 6/2002 | Neev |
| 6,409,720 B1 | 6/2002 | Hissong et al. |
| 6,409,722 B1 | 6/2002 | Hoey et al. |
| 6,413,253 B1 | 7/2002 | Koop et al. |
| 6,413,254 B1 | 7/2002 | Hissong et al. |
| 6,413,255 B1 | 7/2002 | Stern |
| 6,427,089 B1 | 7/2002 | Knowlton |
| 6,428,532 B1 | 8/2002 | Doukas et al. |
| 6,430,446 B1 | 8/2002 | Knowlton |
| 6,436,094 B1 | 8/2002 | Reuter |
| 6,436,127 B1 | 8/2002 | Anderson et al. |
| 6,443,914 B1 | 9/2002 | Costantino |
| 6,443,946 B2 | 9/2002 | Clement et al. |
| 6,451,013 B1 | 9/2002 | Bays et al. |
| 6,451,015 B1 | 9/2002 | Rittman, III et al. |
| 6,457,476 B1 | 10/2002 | Elmer et al. |
| 6,461,378 B1 | 10/2002 | Knowlton |
| 6,468,235 B2 | 10/2002 | Ito et al. |
| 6,470,216 B1 | 10/2002 | Knowlton |
| 6,471,662 B1 | 10/2002 | Jaggy et al. |
| 6,471,696 B1 | 10/2002 | Berube et al. |
| 6,475,179 B1 | 11/2002 | Wang et al. |
| 6,475,211 B2 | 11/2002 | Chess et al. |
| 6,480,746 B1 | 11/2002 | Ingle et al. |
| 6,485,484 B1 | 11/2002 | Connors et al. |
| 6,485,703 B1 | 11/2002 | Cote et al. |
| 6,500,141 B1 | 12/2002 | Irion et al. |
| 6,508,813 B1 | 1/2003 | Altshuler |
| 6,514,250 B1 | 2/2003 | Jahns et al. |
| 6,517,532 B1 | 2/2003 | Altshuler et al. |
| 6,529,778 B2 | 3/2003 | Prutchi |
| 6,558,382 B2 | 5/2003 | Jahns et al. |
| 6,575,969 B1 | 6/2003 | Rittman, III et al. |
| 6,577,903 B1 | 6/2003 | Cronin et al. |
| 6,584,360 B2 | 6/2003 | Francischelli et al. |
| 6,585,733 B2 | 7/2003 | Wellman |
| 6,595,934 B1 | 7/2003 | Hissong et al. |
| 6,600,951 B1 | 7/2003 | Anderson |
| 6,605,080 B1 | 8/2003 | Altshuler et al. |
| 6,607,498 B2 | 8/2003 | Eshel |
| 6,626,854 B2 | 9/2003 | Friedman et al. |
| 6,628,990 B1 | 9/2003 | Habib et al. |
| 6,629,974 B2 | 10/2003 | Penny et al. |
| 6,645,162 B2 | 11/2003 | Friedman et al. |
| 6,648,904 B2 | 11/2003 | Altshuler et al. |
| 6,652,518 B2 | 11/2003 | Wellman et al. |
| 6,653,618 B2 | 11/2003 | Zenzie |
| 6,662,054 B2 | 12/2003 | Kreindel et al. |
| 6,663,659 B2 | 12/2003 | McDaniel |
| 6,676,654 B1 | 1/2004 | Balle Petersen et al. |
| 6,676,655 B2 | 1/2004 | McDaniel |
| 6,682,501 B1 | 1/2004 | Nelson et al. |
| 6,692,450 B1 | 2/2004 | Coleman |
| 6,723,090 B2 | 4/2004 | Altshuler et al. |
| 6,725,095 B2 | 4/2004 | Fenn et al. |
| 6,736,810 B2 | 5/2004 | Hoey et al. |
| 6,743,222 B2 | 6/2004 | Durkin et al. |
| 6,763,836 B2 | 7/2004 | Tasto et al. |
| 6,766,202 B2 | 7/2004 | Underwood et al. |
| 6,807,446 B2 | 10/2004 | Fenn et al. |
| 6,808,532 B2 | 10/2004 | Andersen et al. |
| 6,821,274 B2 | 11/2004 | McHale et al. |
| 6,823,216 B1 | 11/2004 | Salomir et al. |
| 6,824,542 B2 | 11/2004 | Jay |
| 6,856,839 B2 | 2/2005 | Litovitz |
| 6,861,954 B2 | 3/2005 | Levin |
| 6,878,144 B2 | 4/2005 | Altshuler et al. |
| 6,878,147 B2 | 4/2005 | Prakash et al. |
| 6,881,212 B1 | 4/2005 | Clement et al. |
| 6,887,239 B2 | 5/2005 | Elstrom et al. |
| 6,887,260 B1 | 5/2005 | McDaniel |
| 6,888,319 B2 | 5/2005 | Inochkin et al. |
| 6,897,238 B2 | 5/2005 | Anderson |
| 6,907,879 B2 | 6/2005 | Drinan et al. |
| 6,916,316 B2 | 7/2005 | Jay |
| 6,918,908 B2 | 7/2005 | Bonner et al. |
| 6,939,344 B2 | 9/2005 | Kreindel |
| 6,939,346 B2 | 9/2005 | Kannenberg et al. |
| 6,955,672 B2 | 10/2005 | Cense et al. |
| 6,974,415 B2 | 12/2005 | Cerwin et al. |
| 6,976,984 B2 | 12/2005 | Cense et al. |
| 6,997,923 B2 | 2/2006 | Anderson et al. |
| 7,006,874 B2 | 2/2006 | Knowlton et al. |
| 7,022,121 B2 | 4/2006 | Stern et al. |
| 7,029,469 B2 | 4/2006 | Vasily |
| 7,033,352 B1 | 4/2006 | Gauthier et al. |
| 7,044,959 B2 | 5/2006 | Anderson et al. |
| 7,056,318 B2 | 6/2006 | Black |
| 7,066,929 B1 | 6/2006 | Azar et al. |
| 7,074,218 B2 | 7/2006 | Washington et al. |
| 7,081,111 B2 | 7/2006 | Svaasand et al. |
| 7,089,054 B2 | 8/2006 | Palti |
| 7,107,997 B1 | 9/2006 | Moses et al. |
| 7,115,123 B2 | 10/2006 | Knowlton et al. |
| 7,118,590 B1 | 10/2006 | Cronin |
| 7,122,029 B2 | 10/2006 | Koop et al. |

(56) References Cited

U.S. PATENT DOCUMENTS

| | | |
|---|---|---|
| 7,128,739 B2 | 10/2006 | Prakash et al. |
| 7,135,033 B2 | 11/2006 | Altshuler et al. |
| 7,136,699 B2 | 11/2006 | Palti |
| 7,141,049 B2 | 11/2006 | Stern et al. |
| 7,151,964 B2 | 12/2006 | Desai et al. |
| 7,153,256 B2 | 12/2006 | Riehl et al. |
| 7,153,285 B2 | 12/2006 | Lauman et al. |
| 7,163,536 B2 | 1/2007 | Godara |
| 7,175,950 B2 | 2/2007 | Anderson et al. |
| 7,189,230 B2 | 3/2007 | Knowlton |
| 7,192,429 B2 | 3/2007 | Trembly |
| 7,204,832 B2 | 4/2007 | Altshuler et al. |
| 7,217,265 B2 | 5/2007 | Hennings et al. |
| 7,220,254 B2 | 5/2007 | Altshuler et al. |
| 7,220,778 B2 | 5/2007 | Anderson et al. |
| 7,229,436 B2 | 6/2007 | Stern et al. |
| 7,234,739 B2 | 6/2007 | Saitoh et al. |
| 7,238,182 B2 | 7/2007 | Swoyer et al. |
| 7,241,291 B2 | 7/2007 | Kreindel et al. |
| 7,247,155 B2 | 7/2007 | Hoey et al. |
| 7,250,047 B2 | 7/2007 | Anderson et al. |
| 7,252,628 B2 | 8/2007 | Van Hal et al. |
| 7,258,674 B2 | 8/2007 | Cribbs et al. |
| 7,267,675 B2 | 9/2007 | Stern et al. |
| 7,276,058 B2 | 10/2007 | Altshuler et al. |
| 7,290,326 B2 | 11/2007 | Dutton |
| 7,309,335 B2 | 12/2007 | Altshuler et al. |
| 7,311,674 B2 | 12/2007 | Gingrich et al. |
| 7,329,273 B2 | 2/2008 | Altshuler et al. |
| 7,329,274 B2 | 2/2008 | Altshuler et al. |
| 7,331,951 B2 | 2/2008 | Eshel et al. |
| 7,344,587 B2 | 3/2008 | Khan et al. |
| 7,347,855 B2 | 3/2008 | Eshel et al. |
| 7,351,252 B2 | 4/2008 | Altshuler et al. |
| 7,354,448 B2 | 4/2008 | Altshuler et al. |
| 7,367,341 B2 | 5/2008 | Anderson et al. |
| 7,377,917 B2 | 5/2008 | Trembly |
| 7,399,297 B2 | 7/2008 | Ikadai et al. |
| 7,422,586 B2 | 9/2008 | Morris et al. |
| 7,422,598 B2 | 9/2008 | Altshuler et al. |
| 7,431,718 B2 | 10/2008 | Ikadai |
| 7,470,270 B2 | 12/2008 | Azar et al. |
| 7,479,101 B2 | 1/2009 | Hunter et al. |
| 7,481,807 B2 | 1/2009 | Knudsen et al. |
| 7,491,171 B2 | 2/2009 | Barthe et al. |
| 7,524,328 B2 | 4/2009 | Connors et al. |
| 7,530,356 B2 | 5/2009 | Slayton et al. |
| 7,530,958 B2 | 5/2009 | Slayton et al. |
| 7,540,869 B2 | 6/2009 | Altshuler et al. |
| 7,544,204 B2 | 6/2009 | Krespi et al. |
| 7,565,207 B2 | 7/2009 | Turner et al. |
| 7,568,619 B2 | 8/2009 | Todd et al. |
| 7,588,547 B2 | 9/2009 | Deem et al. |
| 7,599,745 B2 | 10/2009 | Palti |
| 7,601,128 B2 | 10/2009 | Deem et al. |
| 7,613,523 B2 | 11/2009 | Eggers et al. |
| 7,630,774 B2 | 12/2009 | Karni et al. |
| 7,643,883 B2 | 1/2010 | Kreindel |
| 7,682,321 B2 | 3/2010 | Naldoni |
| 7,713,234 B2 | 5/2010 | Karanzas |
| 7,722,535 B2 | 5/2010 | Randlov et al. |
| 7,722,600 B2 | 5/2010 | Connors et al. |
| 7,722,656 B1 | 5/2010 | Segal |
| 7,736,360 B2 | 6/2010 | Mody et al. |
| 7,740,600 B2 | 6/2010 | Slatkine et al. |
| 7,740,651 B2 | 6/2010 | Barak et al. |
| 7,749,260 B2 | 7/2010 | Da Silva et al. |
| 7,758,524 B2 | 7/2010 | Barthe et al. |
| 7,758,537 B1 | 7/2010 | Brunell et al. |
| 7,762,964 B2 | 7/2010 | Slatkine |
| 7,763,060 B2 | 7/2010 | Baumann |
| 7,771,421 B2 | 8/2010 | Stewart et al. |
| 7,799,019 B2 | 9/2010 | Turovskiy et al. |
| 7,805,201 B2 | 9/2010 | Palti |
| 7,815,570 B2 | 10/2010 | Eshel et al. |
| 7,815,633 B2 | 10/2010 | Zanelli et al. |
| 7,824,394 B2 | 11/2010 | Manstein |
| 7,828,734 B2 | 11/2010 | Azhari et al. |
| 7,837,694 B2 | 11/2010 | Tethrake et al. |
| 7,842,029 B2 | 11/2010 | Anderson et al. |
| 7,854,754 B2 | 12/2010 | Ting et al. |
| 7,857,773 B2 | 12/2010 | Desilets et al. |
| 7,857,775 B2 | 12/2010 | Rosenberg et al. |
| 7,862,564 B2 | 1/2011 | Goble |
| 7,864,129 B2 | 1/2011 | Konishi |
| 7,891,362 B2 | 2/2011 | Domankevitz et al. |
| 7,905,844 B2 | 3/2011 | Desilets et al. |
| 8,073,550 B1 | 12/2011 | Spertell |
| 8,394,092 B2 * | 3/2013 | Brannan ..................... 606/41 |
| 8,469,951 B2 | 6/2013 | Ben-Haim et al. |
| 8,535,302 B2 | 9/2013 | Ben-Haim et al. |
| 9,028,477 B2 | 5/2015 | Ben-Haim et al. |
| 2001/0005775 A1 | 6/2001 | Samson |
| 2001/0016761 A1 | 8/2001 | Rudie et al. |
| 2001/0050083 A1 | 12/2001 | Marchitto et al. |
| 2002/0062124 A1 | 5/2002 | Keane |
| 2002/0087151 A1 | 7/2002 | Mody et al. |
| 2002/0156471 A1 | 10/2002 | Stern et al. |
| 2002/0165529 A1 | 11/2002 | Danek |
| 2002/0193851 A1 | 12/2002 | Silverman et al. |
| 2003/0004082 A1 | 1/2003 | Masschelein et al. |
| 2003/0006811 A1 | 1/2003 | Oosawa et al. |
| 2003/0032950 A1 * | 2/2003 | Altshuler et al. ................. 606/9 |
| 2003/0130575 A1 | 7/2003 | Desai |
| 2003/0130711 A1 | 7/2003 | Pearson et al. |
| 2003/0158566 A1 | 8/2003 | Brett |
| 2003/0212393 A1 | 11/2003 | Knowlton et al. |
| 2003/0216728 A1 | 11/2003 | Stern et al. |
| 2004/0000316 A1 | 1/2004 | Knowlton et al. |
| 2004/0002705 A1 | 1/2004 | Knowlton et al. |
| 2004/0049251 A1 | 3/2004 | Knowlton |
| 2004/0073115 A1 | 4/2004 | Horzewski et al. |
| 2004/0092875 A1 | 5/2004 | Kochamba |
| 2004/0140028 A1 | 7/2004 | Clark et al. |
| 2004/0186535 A1 | 9/2004 | Knowlton |
| 2004/0206365 A1 | 10/2004 | Knowlton |
| 2004/0210214 A1 | 10/2004 | Knowlton |
| 2004/0230260 A1 | 11/2004 | Macfarland et al. |
| 2004/0243182 A1 | 12/2004 | Cohen et al. |
| 2004/0243200 A1 | 12/2004 | Turner et al. |
| 2004/0249426 A1 | 12/2004 | Hoenig et al. |
| 2005/0010271 A1 | 1/2005 | Merchant |
| 2005/0137654 A1 | 6/2005 | Hoenig et al. |
| 2005/0137662 A1 * | 6/2005 | Morris et al. ................. 607/101 |
| 2005/0215987 A1 | 9/2005 | Slatkine |
| 2005/0251117 A1 | 11/2005 | Anderson et al. |
| 2005/0251120 A1 | 11/2005 | Anderson et al. |
| 2005/0288666 A1 | 12/2005 | Bertolero et al. |
| 2006/0020309 A1 | 1/2006 | Altshuler et al. |
| 2006/0036300 A1 | 2/2006 | Kreindel |
| 2006/0111744 A1 | 5/2006 | Makin et al. |
| 2006/0112698 A1 | 6/2006 | Cazzini et al. |
| 2006/0129209 A1 | 6/2006 | McDaniel |
| 2006/0151485 A1 | 7/2006 | Cronin |
| 2006/0161228 A1 | 7/2006 | Lach |
| 2006/0167498 A1 | 7/2006 | Dilorenzo |
| 2006/0184205 A1 | 8/2006 | Schuler et al. |
| 2006/0189964 A1 | 8/2006 | Anderson et al. |
| 2006/0206110 A1 | 9/2006 | Knowlton et al. |
| 2006/0259102 A1 | 11/2006 | Slatkine |
| 2006/0264926 A1 | 11/2006 | Kochamba |
| 2006/0265034 A1 | 11/2006 | Aknine et al. |
| 2006/0271028 A1 | 11/2006 | Altshuler et al. |
| 2006/0276860 A1 | 12/2006 | Ferren et al. |
| 2007/0010810 A1 | 1/2007 | Kochamba |
| 2007/0016032 A1 | 1/2007 | Aknine |
| 2007/0020355 A1 | 1/2007 | Schlebusch et al. |
| 2007/0049918 A1 | 3/2007 | Van Der Weide et al. |
| 2007/0060989 A1 | 3/2007 | Deem et al. |
| 2007/0078290 A1 | 4/2007 | Esenaliev |
| 2007/0078502 A1 | 4/2007 | Weber et al. |
| 2007/0088413 A1 * | 4/2007 | Weber et al. ..................... 607/99 |
| 2007/0129711 A1 * | 6/2007 | Altshuler et al. ................. 606/9 |
| 2007/0179482 A1 | 8/2007 | Anderson |

(56) References Cited

U.S. PATENT DOCUMENTS

| | | | |
|---|---|---|---|
| 2007/0179535 | A1 | 8/2007 | Morrissey et al. |
| 2007/0233226 | A1 | 10/2007 | Kochamba et al. |
| 2007/0237620 | A1 | 10/2007 | Mühlhoff et al. |
| 2007/0255355 | A1 | 11/2007 | Altshuler et al. |
| 2007/0255362 | A1 | 11/2007 | Levinson et al. |
| 2007/0265585 | A1 | 11/2007 | Joshi et al. |
| 2007/0270925 | A1 | 11/2007 | Levinson |
| 2008/0077201 | A1 | 3/2008 | Levinson et al. |
| 2008/0077202 | A1 | 3/2008 | Levinson |
| 2008/0077211 | A1 | 3/2008 | Levinson et al. |
| 2008/0091183 | A1 | 4/2008 | Knopp et al. |
| 2008/0195000 | A1 | 8/2008 | Spooner et al. |
| 2008/0269851 | A1 | 10/2008 | Deem et al. |
| 2008/0294152 | A1* | 11/2008 | Altshuler et al. ............... 606/9 |
| 2008/0319437 | A1* | 12/2008 | Turner et al. .................. 606/33 |
| 2009/0221999 | A1 | 9/2009 | Shahidi |
| 2009/0299361 | A1 | 12/2009 | Flyash et al. |
| 2009/0299364 | A1 | 12/2009 | Batchelor et al. |
| 2009/0306646 | A1* | 12/2009 | Turner et al. .................. 606/33 |
| 2009/0318917 | A1 | 12/2009 | Leyh et al. |
| 2010/0010480 | A1 | 1/2010 | Mehta et al. |
| 2010/0016782 | A1 | 1/2010 | Oblong |
| 2010/0049178 | A1 | 2/2010 | Deem et al. |
| 2010/0114086 | A1 | 5/2010 | Deem et al. |
| 2010/0211059 | A1 | 8/2010 | Deem et al. |
| 2010/0268220 | A1 | 10/2010 | Johnson et al. |
| 2011/0028898 | A1 | 2/2011 | Clark, III et al. |
| 2011/0196365 | A1 | 8/2011 | Kim et al. |
| 2011/0313412 | A1 | 12/2011 | Kim et al. |
| 2012/0010609 | A1 | 1/2012 | Deem et al. |
| 2012/0022622 | A1 | 1/2012 | Johnson et al. |
| 2012/0041432 | A1 | 2/2012 | Spertell |
| 2012/0265277 | A1* | 10/2012 | Unetich ..................... 607/101 |
| 2013/0066406 | A1 | 3/2013 | Spertell |
| 2013/0150844 | A1 | 6/2013 | Deem et al. |
| 2013/0166003 | A1 | 6/2013 | Johnson et al. |
| 2014/0180271 | A1 | 6/2014 | Johnson et al. |
| 2014/0378959 | A1 | 12/2014 | Spertell |
| 2015/0148792 | A1 | 5/2015 | Kim et al. |

FOREIGN PATENT DOCUMENTS

| | | |
|---|---|---|
| EP | 1346753 A2 | 9/2003 |
| JP | 61-364 A | 1/1986 |
| JP | 62-149347 | 9/1987 |
| JP | S-63177856 A | 7/1988 |
| JP | 07-503874 | 4/1995 |
| JP | H09-239040 | 9/1997 |
| JP | 2001-514921 A | 9/2001 |
| JP | 2006503618 | 2/2006 |
| JP | 2006-289098 | 10/2006 |
| WO | WO 89/02292 A1 | 3/1989 |
| WO | WO 92/07622 A1 | 5/1992 |
| WO | WO 96/23447 A1 | 8/1996 |
| WO | WO 96/41579 A1 | 12/1996 |
| WO | WO 99/46005 A1 | 9/1999 |
| WO | WO 00/24463 A2 | 5/2000 |
| WO | WO 01/58361 A1 | 8/2001 |
| WO | WO 03/039385 A2 | 5/2003 |
| WO | WO 2004/034925 A2 | 4/2004 |
| WO | WO 2005/060354 A2 | 7/2005 |
| WO | WO 2005/099369 A2 | 10/2005 |
| WO | WO 2005/112807 A2 | 12/2005 |
| WO | WO 2005/120379 A2 | 12/2005 |
| WO | WO 2006/089227 A2 | 8/2006 |
| WO | WO 2006/090217 A1 | 8/2006 |
| WO | WO 2006/117682 A2 | 11/2006 |
| WO | WO 2006/122136 A2 | 11/2006 |
| WO | WO 2007/015247 A2 | 2/2007 |
| WO | WO 2007/030367 A2 | 3/2007 |
| WO | WO 2007/038567 A1 | 4/2007 |
| WO | WO 2007/050572 A2 | 5/2007 |
| WO | WO 2007/106339 A2 | 9/2007 |
| WO | WO 2007/108516 A1 | 9/2007 |
| WO | WO 2007/131112 A2 | 11/2007 |
| WO | WO 2007/140469 A2 | 12/2007 |
| WO | WO 2009/072108 A2 | 6/2009 |

OTHER PUBLICATIONS

Absar et al.; Efficacy of botulinum toxin type A in the treatment of focal axillary hyperhidrosis; Dermatol Surg; 34(6); pp. 751-755; Jun. 2008.

Acculis; Microwave Ablation for Healthcare Professionals; 2 pgs.; accessed Jun. 24, 2008; (http://www.acculis.com/mta).

Aesthera US—How it Works; 2 pgs.; accessed Jul. 8, 2008 (http://www.aesthera.com/go/aestheralUS/patients/how_it_works/index.cfm).

Alster et al.; Improvement of neck and cheek laxity with a non-ablative radiofrequency device: a lifting experience; Dermatol Surg; 30(4); pp. 503-507; Apr. 2004.

Ashby et al.; Cryosurgery for Axillary Hyperhidrosis; British Medical Journal Short Reports; London; pp. 1173-1174; Nov. 13, 1976.

Atkins et al.; Hyperhidrosis: A Review of Current Management; Plast Reconstr Surg; 110(1); pp. 222-228; Jul. 2002.

Ball, P.; Radio sweat gland—90 GHz; Nature; 452(7188); p. 676; Apr. 10, 2008; printed Jun. 18, 2012 from website (http://www.nature.com/news/2008/080409/full/452676a.html).

Basra et al.; The dermatology life quality index 1994R2007: A comprehensive review of validation data and clinical results; Br J Dermatol;159(5); pp. 997R1035; Nov. 2008.

Beer et al., Immunohistochemical Differentiation and Localization Analysis of Sweat Glands in the Adult Human Axilla, Plastic and Reconstructive Surgery, vol. 117, No. 6, pp. 2043-2049, May 2006.

Bindu et al.; Microwave characterization of breast-phantom materials; Microwave and Optical Tech. Letters; 43(6); pp. 506-508; Dec. 20, 2004.

Bioportfolio; Tenex Health Receives FDA clearance for innovative TX1) tissue removal system; 2 pgs.; release dated Mar. 9, 2011; printed on Jun. 18, 2012 from website (http://www.bioportfolio.com/news/article/519143/Tenex-Health-Receives-Fda-Clearance-For-Innovative-Tx1-Tissue-Removal-System.html).

Brace et al., Microwave Ablation with a Trixial Antenna: Results in ex vivo Bovine Liver, IEEE transactions on Microwave Theory and Techniques, vol. 53, No. 1, pp. 215-220 (Jan. 2005).

BSD Medical Corporation; Hyperthermia therapy contributes to 85 percent survival rate from childhood cancers; 2 pgs.; Jan. 13, 2009; printed Jun. 18, 2009 from website (http://www.irconnect.com/noc/press/pages/news_releases.html?d=157551).

Bu-Lin et al.; A polyacrylamide gel phantom for radiofrequency ablation; Int. J. Hyperthermia; 24(7); pp. 568-576; Nov. 2008.

Burns, Jay A.; Thermage: monopolar radiofrequency; Aesthetic Surg J; 25(6); pp. 638-642; Nov./Dec. 2005.

Campbell et al.; Dielectric properties of female human breast tissue measured in vitro at 3.2 GHz; Phys. Med. Biol.; 37(1); pp. 193-210; Jan. 1992.

Candela Corp.; The Candela SeleroPLUS Laser with Dynamic Cooling Device: The Benefits of Anesthesia without the Risks; Nov. 1998.

Chang et al.; A conductive plastic for simulating biological tissue at microwave frequencies; IEEE Trans on Electromagnetic Compatibility; 42(1); pp. 76-81; Feb. 2000.

Christ et al., Characterization of the Electromagnetic Near-Field Absorption in Layered Biological Tissue in the Frequency Range from 30 MHz to 6000 MHz, Phys. Med. Biol. 51, pp. 4951-4965; Oct. 2006.

Christ et al., The Dependence of Electromagnetic Far-Field Absorption on Body Tissue Composition in the Frequency Range from 300 MHz to 6 GHz, IEEE Transactions on Microwave Theory and Techniques, vol. 54, No. 5, pp. 2188-2195 (May 2006).

CK Electronic GmbH; Scientific Measurements of Skin and Hair (product information); 15 pgs.; published after Sep. 2006.

Copty et al., Low-power near-field microwave applicator for localized heating of soft matter, Applied Physics Letters, vol. 84, No. 25, pp. 5109-5111 (Jun. 21, 2004).

Covidien; FDA clears Covidien's Evident} microwave ablation system for use in nonresectable liver tumor ablation; 2 pgs.; Dec. 28,

(56) References Cited

OTHER PUBLICATIONS

2008; printed Jun. 18, 2012 from website (http://www.medicalnewstoday.com/releases/133800.php).
Darabaneanu et al.; Long-term efficacy of subcutaneous sweat gland suction curettage for axillary hyperhidrosis: a prospective gravimetrically controlled study; Dermatol Surg; 34(9); pp. 1170-1177; Sep. 2008.
De Bruijne et al., Effects of waterbolus size, shape and configuration on the SAR distribution pattern of the Lucite cone applicator, International Journal of Hyperthermia, 22(1): 15-28 (Feb. 2006).
Dewey; Arrhenius relationships from the molecule and cell to the clinic; Int. J. Hyperthermia; 25(1); pp. 3-20; Feb. 2009.
Diederich et al.; Pre-clinical Evaluation of a Microwave Planar Array Applicator for Superficial Hyperthermia; International Journal of Hyperthermia; vol. 9, No. 2; pp. 227-246; Jan. 1993.
Drozd et al.; Comparison of Coaxial Dipole Antennas for Applications in the Near-Field and Far-Field Regions; MW Journal, vol. 47, No. 5 (May 2004), http://www.mwjournal.com/Journal, accessed Dec. 10, 2007.
Eleiwa et al.; Accurate FDTD simulation of biological tissues for bio-electromagnetic applications; IEEE Proc. SoutheastCon 2001; Clemson, SC; Mar. 30-Apr. 1, 2001; pp. 174-178.
Farace et al.; An automated method for mapping human tissue permittivities by MRI in hyperthermia treatment planning; Phys. Med. Biol.; 42(11); pp. 2159-2174; Nov. 1997.
Fitzpatrick et al.; Multicenter study of noninvasive radiofrequency for periorbital tissue tightening; Lasers Surg Med; 33(4); pp. 232-242; Mar. 2003.
Gabriel et al.; Dielectric parameters relevant to microwave dielectric heating; Chem Soc Rev; 27(3); pp. 213R224; May-Jun. 1998.
Gabriel et al.; The dielectric properties of biological tissues: I. Literature survey; Phys Med Biol; 41(11); pp. 2231R2249; Nov. 1996.
Gabriel et al.; The dielectric properties of biological tissues: II. Measurements in the frequency range 10 Hz to 20 GHz; Phys Med Biol; 41(11); pp. 2251R2269; Nov. 1996.
Gabriel et al.; The dielectric properties of biological tissues: III. Parametric models for the dielectric spectrum of tissues; Phys Med Biol; 41(11); pp. 2271R2293; Nov. 1996.
Gabriel, et al.; Comparison of the Dielectric Properties of Normal and Wounded Human Skin Material; Bioelectromagnetics; 8; pp. 23-27; Jan. 1987.
Gandhi et al.; Electromagnetic Absorption in the Human Head and Neck for Mobile Telephones at 835 and 1900 MHz; IEEE Transactions on Microwave Theory and Techniques; 44(10); pp. 1884R1897; Oct. 1996.
Garber, B. B.; Office microwave treatment of enlarged prostate symptoms; 2 pgs.; printed from website (http://www.garber-online.com/microwave-treatment.htm) on Jun. 18, 2012.
Gold et al.; Treatment of Wrinkles and Skin Tightening Using Aluma(TM) Skin Renewal System with FACES (TM)(Functional Aspiration Controlled Electrothermal Stimulation) Technology; Lumens, Inc. (Oct. 2005).
Goldman et al.; Subdermal Nd-YAG laser for axillary hyperhidrosis; Dermatol Surg; 34(6); pp. 756-762; Jun. 2008.
Guidant Corp.; Guidant microwave surgical ablation system; 1 pg.; © 2004; printed Jun. 18, 2012 from website (http://web.archive.org/web/20070306031424/http://www.ctsnet.org/file/vendors/872/pdf/MicrowaveAblationIFU.pdf).
Guy, Arthur; History of Biological Effects and Medical Applications of Microwave Energy; IEEE Transactions on Microwave Theory and Techniques; 32(9); pp. 1182-1200; Sep. 1984.
Guy, Arthur; Therapeutic Heat and Cold, Fourth Ed.; Chapter 5: Biophysics of High-Frequency Currents and Electromagnetic Radiation; pp. 179R236. Williams and Wilkins (publishers); Apr. 1990.
Guy; Analyses of electromagnetic fields induced in biological tissues by thermographic studies on equivalent phantom models; IEEE Trans on Microwave Theory and Techniques; MTT-19(2); pp. 205-214; Feb. 1971.
Hey-Shipton, et al.; The Complex Permittivity of Human Tissue at Microwave Frequencies; Phys. Med. Biol.; 27(8); pp. 1067-1071; Aug. 1982.
Hisada et al.; Hereditary Hemorrhagic Telangiectasia Showing Severe Anemia which was successfully treated with estrogen; International Medicine; vol. 34; No. 6; pp. 589-592; Jun. 1995.
Hodgkinson, D. J.; Clinical applications of radiofrequency: nonsurgical skin tightening (thermage); Clin Plastic Surg; 36(2); pp. 261-268; Apr. 2009.
Hu, Da Zhang, Electromagnetic Field in Organism of Skin-Fat-Muscle, China Research Institute of Radiowave Propagation IEEE, pp. 807-812 (Aug. 1998).
Jacobsen et al.; Characteristics of microstrip muscle-loaded single-arm archimedean spiral antennas as investigated by FDTD numerical computations; IEEE Trans. On Biomedical Engineering; 52(2); pp. 321-330; Feb. 2005.
Jacobsen et al.; Characterization of a tranceiving antenna concept for microwave heating and thermometry of superficial tumors; PIER; vol. 18; pp. 105-125; (month unavailable) 1998.
Jacobsen et al.; Dual-mode antenna design for microwave heating and noninvasive thermometry of superficial tissue disease; IEEE Trans. On Biomedical Engineering; 47(11); pp. 1500-1509; Nov. 2000.
Jacobsen et al.; Multifrequency radiometric determination of temperature profiles in a lossy homogeneous phantom using a dual-mode antenna with integral water bolus; IEEE Trans. on Microwave Theory and Techniques; 50(7); pp. 1737-1746; Jul. 2002.
Jacobsen et al.; Nonparametric 1-D temperature restoration in lossy media using tikhonov regularization on sparse radiometry data; IEEE Trans. on Biomedical Engineering; 50(2); pp. 178-188; Feb. 2003.
Jacobsen et al.; Transceiving antenna for homogenious heating and radiometric thermometry during hyperthermia; Electronic Letters; 36(6); pp. 496-497; Mar. 16, 2000.
Johnson et al.; Automatic temperature controller for multielement array hyperthermia systems; IEEE Trans. on Biomedical Engineering; 53(6); pp. 1006-1015; Jun. 2006.
Johnson et al.; Evaluation of a dual-arm Archimedean spiral array for microwave hyperthermia; Int J Hyperthermia; 22(6); pp. 475R490; Sep. 2006.
Juang et al.; Construction of a conformal water bolus vest applicator for hyperthermia treatment of superficial skin cancer; Proc. of the 26th Ann. Int. Conf. of the IEEE EMBS; San Francisco, CA, USA; Sep. 1-5, 2004; pp. 3467-3470.
Kawoos et al., Issues in Wireless Intracranial Pressure Monitoring at Microwave Frequencies, PIERS Online, vol. 3, No. 6, pp. 927-931; 2007 (month unavailable).
Kirn, T. F.; Researchers seek to quantify thermage efficacy; Dermatologic Surgery; p. 36; Jan. 2007.
Kirsch et al.; Ultrastructure of collagen thermally denatured by microsecond domain pulsed carbon dioxide laser; Arch Dermatol; 134; pp. 1255-1259; Oct. 1998.
Kobayashi, T.; Electrosurgery Using Insulated Needles: Treatment of Axillary Bromhidrosis and Hyperhidrosis; Journal of Dermatologic Surgery & Oncology; 14(7) pp. 749-752; Jul. 1988.
Krusen, Frank (M.D.); Samuel Hyde Memorial Lecture: Medical Applications of Microwave Diathermy: Laboratory and Clinical Studies. Proceedings of the Royal Society of Medicine; 43(8); pp. 641-658, May 10, 1950.
Kumaradas et al.; Optimization of a beam shaping bolus for superficial microwave hyperthermia waveguide applicators using a finite element method; Phys. Med. Biol.; 48(1); pp. 1-18; Jan. 7, 2003.
Lagendijk et al; Hyperthermia dough: a fat and bone equivalent phantom to test microwave/radiofrequency hyperthermia heating systems; Phys. Med. Biol.; 30(7); pp. 709-712; Jul. 1985.
Land et al.; A quick accurate method for measuring the microwave dielectric properties of small tissue samples; Phys. Med. Biol.; 37(1); pp. 183-192; Jan. 1992.
Lane et al.; Pressure-Induced Bullae and Sweat Gland Necrosis Following Chemotherapy Induction; The American Journal of Medicine; vol. 117; pp. 441-443; Sep. 15, 2004.
Larson et al.; Microwave treatments for enlared prostate cause blood pressure surges, study shows; 2 pgs.; Apr. 11, 2008; printed on Jun.

(56) References Cited

OTHER PUBLICATIONS 18, 2012 from website (http://web.archive.org/web/20080415000815/http://www.sciencedaily.com/releases/2008/04/080408105820.htm).

Lawrence et al.; Selective Sweat Gland Removal with Minimal Skin Excision in the Treatment of Axillary Hyperhidrosis: A Retrospective Clinical and Histological Review of 15 Patients; British Journal of Dermatology; British Association of Dermatologists; 155(1), pp. 115-118; Jul. 2006.

Lehmann et al.; Therapeutic Heat; Therapeutic Heat and Cold, Fourth Ed.; Chapter 9; pp. 417-581; Williams & Wilkins (publishers), Baltimore, MD; Apr. 1990.

Lowe et al.; Microwave delivery system for lower leg telangiectasia; Journal of Cutaneous Laser Therapy; 2(1); pp. 3-7; Mar. 2000.

Lumenis Inc.; Aluma RF Skin Renewal System (product information); copyright 2007 (PB-1013670); 8 pgs.; Oct. 2007 (printed version).

Maccarini et al.; Advances in microwave hyperthermia of large superficial tumors; Microwave Symposium Digest, IEEE MTT-S International; pp. 1797-1800; Jun. 2005.

Maccarini et al.; Electromagnetic optimization of dual mode antennas for radiometry controlled heating of superficial tissue; Proceedings of SPIE; vol. 5698; Bellingham, WA; pp. 71-81; Jan. 2005.

Maccarini et al.; Optimization of a dual concentric conductor antenna for superficial hyperthermia applications; Proc. of the 26th Ann. Int. Conf. of the IEEE EMBS; San Francisco, CA, USA; Sep. 1-5, 2004; pp. 2518-2521.

Mazzurana et al.; A semi-automatic method for developing an anthropomorphic numerical model of dielectric anatomy by MRI; Phys. Med. Biol.; 48(19); pp. 3157-3170; Oct. 7, 2003.

Michel et al.; Design and Modeling of Microstrip—Microslot Applicators with Several Patches and Apertures for Microwave Hyperthermia; Microwave and Optical Technology Letters; vol. 14, No. 2; pp. 121-125; Feb. 5, 1997.

Mrozowski et al.; Parameterization of media dispersive properties for FDTD; IEEE Trans on Antennas and Propagation; 45(9); pp. 1438-1439; Sep. 1997.

Nagaoka et al.; Development of realistic high-resolution whole-body voxel models of Japanese adult males and females of average height and weight, and application of models to radio-frequency electromagnetic-field dosimetry; Phys. Med. Biol.; 49(1); pp. 1-15; Jan. 7, 2004.

Neuman; SAR pattern perturbations from resonance effects in water bolus layers used with superficial microwave hyperthermia applicators; Int. J. Hyperthermia; 18(3); pp. 180-193; May-Jun. 2002.

Park et al.; A Comparative Study of the Surgical Treatment of Axillary Osmidrosis by Instrument, Manual, and Combined Subcutaneous Shaving Procedures; 41(5); pp. 488-497; Nov. 1998.

Paulides et al.; A Patch Antenna Design for Application in a Phased-Array Head and Neck Hyperthermia Applicator; IEEE Transactions on Biomedical Engineering; 54(11); pp. 2057-2063; Nov. 2007.

Popovic et al.; Dielectric spectroscopy of breast tissue—improved model of the precision open-ended coaxial probe; Proc of the 25th Ann Int Conf of the IEEE EMBS; Cancun, Mexico; pp. 3791-3793; Sep. 17-21, 2003.

Popovic et al.; Response characterization of the precision open-ended coaxial probe for dielectric spectroscopy of breast tissue; 2003 IEEE—Anntennas and Propagation Soc. Int. Symp.; vol. 4; pp. 54-57; Jun. 22-27, 2003.

Pozar, David M.; Electromagnetic Theory (Introduction); Microwave Engineering, Second Edition; John Wiley & Sons, Inc.; p. 1; Aug. 1997.

Rappaport, C.; Treating Cardiac Disease with Catheter-Based Tissue Heating; IEEE Microwave Magazine; 3(1); pp. 57-64; Mar. 2002.

Rolfsnes et al.; Design of spiral antennas for radiometric temperature measurement; Proc. of the 26th Ann. Int. Conf. of the IEEE EMBS; San Francisco, CA, USA; Sep. 1-5, 2004; pp. 2522-2525.

Rosen et al.; Microwaves treat heart disease; IEEE Microw Mag; 8(1); pp. 70R75; Feb. 2007.

Ross et al.; A pilot study of in vivo immediate tissue contraction with CO2 skin laser resurfacing in a live farm pig; Dermatol Surg; 25(11); pp. 851R856; Nov. 1999.

Ross et al.; Comparison of carbon dioxide laser, erbium: Yag laser, dermabrasion, and dermatome A study of thermal damage, wound contraction, and woundhealing in a live pig model: Implications for skin. resurfacing; J Am Acad Dermatol; 42(1); pp. 92R105; Jan. 2000.

Ross et al.; Use of a novel erbium laser in a yucatan minipig: A study of residual thermal damage, ablation, and wound healing as a function of pulse duration; Lasers Surg Med; 30(2); pp. 93R100; Feb. 2002.

Rossetto et al.; Effect of complex bolus-tissue load configurations on SAR distributions from dual concentric conductor applicators; IEEE Trans. on Biomedical Engineering; 46(11); pp. 1310-1319; Nov. 1999.

Saito et al.; Clinical Trials of Interstitual Microwave Hyperthermia by Use of Coaxial-Slot Antenna With Two Slots; IEEE Trans. on Microwave Theory and Techniques; vol. 52; No. 8; pp. 1987-1991; Aug. 2004.

Sherar et al.; Helical antenna arrays for interstitial microwave thermal therapy for prostate cancer: tissue phantom testing and simulations for treatment; Physics in Medicine and Biology; 46(7); pp. 1905-1918; Jul. 2001.

Shimm, D et al.; Hyperthermia in the Treatment of Malignancies; Therapeutic Heat and Cold Fourth Edition edited by Justin Lehmann M.D., Chapter 14, pp. 674-699, Williams & Wilkins Publishers, Baltimore, MD; Apr. 1990.

Sipahioglu et al.; Dielectric properties of vegetables and fruits as a function of temperature, ash, and moisture content; Journal of Food Science; 68(1); pp. 234-239; Jan. 2003.

Surowiec et al.; Dielectric properties of breast carcinoma ind the surrounding tissues; IEEE Trans on Biomedical Engineering; 35(4); pp. 257-263; Apr. 1988.

Solta Medical, Inc.; Study Published in Facial Plastic Surgery Journal Finds Selective Heating of Fibrous Septae Key to Success and Safety of Thermage(R) ThermaCool(TM) System; Thermage® Press Release; 2 pgs.; Jun. 20, 2005.

Spertell et al.; Review of clinical data on hair removal using the MW 2000 microwave delivery system (promotional material); 2000; MW Medical, Inc.; printed from http://www.hairfacts.com/medpubs/mwave/spertell.html on Jun. 23, 2009; 5 pgs.

Spertell; Presentation at the American Academy of Dermatology; MW Medical, Inc.; Mar. 10, 2000; 21 pgs.

Spertell; The application of microwaves to the treatment of cosmetic skin conditions: a technical summary; MW Medical, Inc.; pp. 1-15; May 25, 1999.

SRLI Technologies; BTC-2000} (product information); printed from website: http://www.srli.com/technologies/BTC2000.html on Nov. 16, 2009; 1 pg.

Stauffer et al.; Combination applicator for simultaneous heat and radiation; Proc. of the 26th Ann. Int. Conf. of the IEEE EMBS; San Francisco, CA, USA; Sep. 1-5, 2004; pp. 2514-2517.

Stauffer et al.; Dual mode antenna array for microwave heating and non-invasive thermometry of superficial tissue disease; SPIE Conf. on Thermal Treatment of Tissue with Image Guidance; San Jose, CA; SPIE; vol. 3594; pp. 139-147; Jan. 1999.

Stauffer et al.; Microwave array applicator for rediometry controlled superficial hyperthermia; Proc. of the SPIE; vol. 4247; pp. 19-29; Jun. 2001.

Stauffer et al.; Phantom and animal tissues for modelling the electrical properties of human liver; Int. J. Hyperthermia; 19(1); pp. 89-101; Jan.-Feb. 2003.

Stauffer et al.; Practical induction heating coil designs for clinical hyperthermia with ferromagnetic implants; IEEE Trans. on Biomedical Engineering; 41(1); pp. 17-28; Jan. 1994.

Stauffer et al.; Progress on system for applying simultaneous heat and brachytherapy to large-area surface disease; Proceedings of SPIE; vol. 5698; Bellingham, WA; pp. 82-96; Jan. 2005.

Stauffer et al.; Progress toward radiometry controlled conformal microwave array hyperthermia applicator; Proc. of the 22nd Ann. EMBS Int. Conf.; Chicago, IL; Jul. 23-28, 2000; pp. 1613-1616.

(56) References Cited

OTHER PUBLICATIONS

Stauffer, Paul R.; Evolving technology for thermal therapy of cancer; International Journal of Hyperthermia; 21(8); pp. 731-744; Dec. 2005.

Stauffer, Paul R.; Thermal Therapy Techniques for Skin and Superficial Tissue Disease; Critical Reviews; SPIE Optical Engineering Press (Bellingham, WA); vol. CR75; pp. 327-367; Jan. 2000.

Sterzer, Fred, Microwave Medical Devices; IEEE Microwave Magazine, 3(1); pp. 65-70; Mar. 2002.

Stoy et al.; Dielectric properties of mammalian tissues from 0.1 to 100 MHz: a summary of recent data; Phys. Med. Bil.; 27(4); pp. 501-513; Apr. 1982.

Strutton et al.; US prevalence of hyperhidrosis and impact on individuals with axillary hyperhidrosis: Results from a national survey. J Am Acad Dermatol; 51(2); pp. 241R248; Feb. 2004.

Stuchly et al.; Diathermy applicators with circular aperture and corrugated flange; IEEE Trans on Microwave Theory and Techniques; MTT-28(3); pp. 267-271; Mar. 1980.

Stuchly et al.; Dielectric properties of animal tissues in vivo at frequencies 10 MHz—1 GHz; Bioelectromagnetics; 2(2); pp. 93-103; Apr. 1981.

Stuchly et al.; Dielectric properties of animal tissues in vivo at radio and microwave frequencies: comparison between species; Phys. Med. Biol.; 27(7); pp. 927-936; Jul. 1982.

Sullivan et al.; Comparison of measured and simulated data in an annular phased array using an inhomogeneous phantom; IEEE Trans on Microwave Theory and Techniques; 40(3); pp. 600-604; Mar. 1992.

Sullivan et al.; The pig as a model for human wound healing; Wound Repair Regen; 9(2); pp. 66R76; Mar. 2001.

Sunaga et al.; Development of a dielectric equivalent gel for better impedance matching for human skin; Bioelectromagnetics; 24; pp. 214-217; Apr. 2003.

Tavernier et al.; Conductivity and dielectric permittivity of dermis and epidermis in nutrient liquid saturation; Engineering in Medicine and Biology Society; 1992 14th Annual Int. Conf of the IEEE; Paris, France; pp. 274-275; Oct. 29-Nov. 1, 1992.

Thermolase Corp.; 510K Pre-Market Notification (No. K950019) and Product User Manual ThermoLase Model LT100 Q-Switched Nd: YAG, Laser Hair Removal System, Jan. 3, 1995.

Trembly et al.; Combined Microwave Heating and Surface Cooling of the Cornea; IEEE Transactions on Biomedical Engineering; vol. 38; No. 1; pp. 85-91; Jan. 1991.

Urolgix, Inc.; Cooled Thermotherapy + Prostiva RF = Durability + Versatility; 1 pg.; printed Jun. 18, 2012 from website (http://www.urologix.com/).

Uzunoglu et al.; A 432-MHz Local Hyperthermia System Using an Indirectly Cooled, Water-Loaded Waveguide Applicator; IEEE Trans. on Microwave Theory and Techniques; vol. 35, No. 2; pp. 106-111; Feb. 1987.

Valleylab; Cool-tip} RF Ablation System; (http://www.cool-tiprf.com/physics.html) accessed Jun. 24, 2008.

Van Rhoon et al.; A 433 MHz Lucite Cone Waveguide Applicator for Superficial Hyperthermia; International Journal of Hyperthermia; vol. 14, No. 1; pp. 13-27; Jan.-Feb. 1998.

Vander Vorst et al.; RF/microwave interaction with biological tissues; Hoboken, NJ; John Wiley & Sons, Inc.; pp. 264-305; Jan. 2006.

Vardaxis et al.; Confocal laser scanning microscopy of porcine skin: Implications for human wound healing studies; J Anat; 190(04); pp. 601R611; May 1997.

Vrba, et al.; Evanescent-Mode Applicators (EMA) for Superficial and Subcutaneous Hyperthermia; IEEE Trans. on Biomedical Engineering; vol. 40; No. 5; pp. 397-407; May 1993.

Weiss et al.; Monopolar radiofrequency facial tightening: a retrospective analysis of efficacy and safety in over 600 treatments; J Drugs Dermatol; 5(8); pp. 707-712; Sep. 2006.

Wollina et al.; Tumescent suction curettage versus minimal skin resection with subcutaneous curettage of sweat glands in axillary hyperhidrosis; Dermatol Surg; 34(5); pp. 709-716; May 2008.

Wonnell et al.; Evaluation of microwave and radio frequency catheter ablation in a myocardium-equivalent phantom model; IEEE Trans. on Biomedical engineering; 39(10); pp. 1086-1095; Oct. 1992.

Yang et al.; A Floating Sleeve Antenna Yields Localized Hepatic Microwave Ablation; IEEE Transactions on Biomedical Engineering; 53(3); pp. 533-537; Mar. 2006.

Zelickson et al.; Histological and ultrastructural evaluation of the effects of a radiofrequency-based nonablative dermal remodeling device; Arch Dermatol; 140; pp. 204-209; Feb. 2004.

Zelickson et al.; Ultrastructural effects of an infrared handpiece on forehead and abdominal skin; Dermatol Surg; 32(7); pp. 897-901; Jul. 2006.

Zhou et al.; Resection of Meningiomas with Implantable Microwave Coagualation; Bioelectromagnetics; vol. 17; No. 2; pp. 85-88; (month unavailable) 1996.

Ben-Haim et al.; U.S. Appl. No. 13/563,656 entitled "Applicator and Tissue Interface Module for Dermatological Device," filed Jul. 31, 2012.

Allergan Pharmaceuticals; Botox® (product insert); 16 pgs.; Oct. 2006.

Arneja et al.; Axillary hyperhidrosis: a 5-year review of treatment efficacy and recurrence rates using a new arthroscopic shaver technique; Plast. Reconstr. Surg.; vol. 119; pp. 562-567; Feb. 2007.

Bechara et al.; Histological and clinical findings in different surgical strategies for focal axillary hyperhidrosis; Dermatol Surg; vol. 34; pp. 1001-1009; Aug. 2008.

Bentel et al.; Variability of the depth of supraclavicular and axillary lymph nodes in patients with breast cancer: is a posterior axillary boost field necessary?; Int J Radiation Oncology Biol Phys; vol. 47(3); pp. 755-758; Jun. 2000.

Blanchard et al.; Relapse and morbidity in patients undergoing sentinel lymph node biopsy alone or with axillary dissection for breast cancer; Arch Surg; vol. 138; pp. 482-488; May 2003.

Cobham; Antenna & Radome Design Aids (product list); 1 pg.; Aug. 2001.

Commons et al.; Treatment of axillary hyperhidrosis/bromidrosis using VASER ultrasound; Aesth Plast Surg; vol. 33(3); pp. 312-323; May 2009 (pub'd online Jan. 3, 2009).

Duparc et al.; Anatomical basis of the variable aspects of injuries of the axillary nerve (excluding the terminal branches in the deltoid muscle); Surg Radiol Anat; vol. 19(3); pp. 127-132; May 1997.

Galloway et al.; Ultrasound imaging of the axillary vein—anatomical basis for central venous access; British ournal of Anaesthesia; 90(5); pp. 589-595; May 2003.

Haedersdal et al.; Evidence-based review of hair removal using lasers and light sources; JEADV; vol. 20; pp. 9-20; Jan. 2006.

Hornberger et al.; Recognition, diagnosis, and treatment of primary focal hyperhidrosis; J Am Acad Dermatol; vol. 51; pp. 274-286; Aug. 2004.

Lowe et al.; Botulinum toxin type A in the treatment of primary axillary hyperhidrosis: A 52-week multicenter double-blind, randomized, placebo-controlled study of efficacy and safety; J Am Acad Dermatol; vol. 56; pp. 604-611; Apr. 2007.

Riddle et al.; Complex permittivity measurements of common plastics over variable temperatures; IEEE Trans on Microwave Theory and Techniques; vol. 51(3); pp. 727-733; Mar. 2003.

Solish et al.; A comprehensive approach to the recognition, diagnosis, and severity-based treatment of focal hyperhidrosis: recommendations of the Canadian hyperhidrosis advisory committee; Dermatol Surg; vol. 33; pp. 908-923; Aug. 2007.

Solish et al.; Prospective open-label study of botulinum toxin type A in patients with axillary hyperhodrosis: effects on functional impairment and quality of life; Dermatol Surg; vol. 31(4); pp. 405-413; Apr. 2005.

Wikipedia; Bayonet mount; 6 pages; Dec. 18, 2014; retrieved from the internet (www.http://en.wikipedia.org/wiki/Bayonet mount).

Wikipedia; ISM band; 5 pages; printed Jul. 22, 2014 from website (http://en.wikipedia.org/wiki/ISM_band).

Gabriel; Compilation of the dielectric properties of body tissues at RF and microwave frequencies (Technical Report); Armstrong Laboratory; Doc. No. AL/OE-TR-1996-004; pp. 1-16; Jan. 1996.

(56) References Cited

OTHER PUBLICATIONS

Gandhi et al.; Electromagnetic Absorption in the Human Head from Experimental 6-GHz Handheld Transceivers; IEEE Trans. On Electromagnetic Compatibility; 37(4); pp. 547-558; Nov. 1995.

Houzen et al.; Implanted antenna for an artificial cardiac pacemaker system; Progress in Electromagnetics Research Symposium 2007; Prague, CZ; pp. 51-54; Aug. 27-30, 2007.

Kim et al.; Implanted antennas inside a human body: Simulations, designs, and characterizations; IEEE Trans on Microwave Theory and Techniques; 52(8); pp. 1934-1943; Aug. 2004.

Klemm et al.; EM energy absorption in the human body tissues due to UWB antennas; Progress in Electromagnetics Research; Pier; 62; pp. 261-280; 2006 (year of pub. sufficiently earlier than effective US filed and any foreign priority date).

Soontornpipit et al.; Design of implantable microstrip antenna for communication with medical implants; IEEE Trans on Microwave Theory and Techniques; 52(8); pp. 1944-1951; Aug. 2004.

Virga et al.; Low-profile enhanced-bandwidth PIFA antennas for wireless communications packaging; IEEE Trans on Microwave Theory and Techniques; 45(10); pp. 1879-1888; Oct. 1997.

Warty et al.; Characterization of implantable antennas for intracranial pressure monitoring: reflection by and transmission through a scalp phantom; IEEE Trans on Mircrowave Theory and Techniques; 56(10); pp. 2366-2376; Oct. 2008.

Wright et al.; Hepatic microwave ablation with multiple antennae results in synergistically larger zones of coagulation necrosis; Ann. Surg. Oncol.; 10(3); pp. 275-283; Apr. 2003.

Deem et al.; U.S. Appl. No. 14/740,934 entitled "Methods and apparatus for reducing sweat production," filed Jun. 16, 2015.

* cited by examiner

A-A

SYSTEMS, APPARATUS, METHODS AND PROCEDURES FOR THE NONINVASIVE TREATMENT OF TISSUE USING MICROWAVE ENERGY

RELATED APPLICATIONS

This application claims the benefit of U.S. Provisional Patent Application Ser. No. 61/208,315, filed Feb. 23, 2009, and entitled "Systems, Apparatus, Methods And Procedures For The Noninvasive Treatment Of Tissue Using Microwave Energy," which is expressly incorporated herein by reference in its entirety.

This application also claims the benefit of PCT Application Serial No. PCT/US2008/013650, filed Dec. 12, 2008, and entitled "Systems, Apparatus, Methods And Procedures For The Noninvasive Treatment Of Tissue Using Microwave Energy," which is expressly incorporated herein by reference in its entirety.

This application also claims the benefit of U.S. Provisional Patent Application Ser. No. 61/196,948, filed Oct. 22, 2008, and entitled "Systems And Methods For Creating An Effect Using Microwave Energy To Specified Tissue, Such As Sweat Glands," which is expressly incorporated herein by reference in its entirety.

This application also is a continuation-in-part of co-pending U.S. patent application Ser. No. 12/107,025, filed Apr. 21, 2008, and entitled "Systems And Methods For Creating An Effect Using Microwave Energy To Specified Tissue," which claims the benefit of each of U.S. Provisional Patent Application Ser. No. 60/912,899, filed Apr. 19, 2007, and entitled "Methods And Apparatus For Reducing Sweat Production;" and U.S. Provisional Patent Application Ser. No. 61/013,274, filed Dec. 12, 2007, and entitled "Methods, Devices And Systems For Non-Invasive Delivery Of Microwave Therapy;" and U.S. Provisional Patent Application Ser. No. 61/045,937, filed Apr. 17, 2008, and entitled "Systems And Methods For Creating An Effect Using Microwave Energy In Specified Tissue." All of the above priority applications are expressly incorporated by reference in their entirety.

Co-pending U.S. patent application Ser. No. 12/107,025 also claims priority to each of PCT Application Serial. No. PCT/US08/60935, filed Apr. 18, 2008, and entitled "Methods And Apparatus For Sweat Production"; and PCT Application Serial No. PCT/US08/60929, filed Apr. 18, 2008, and entitled "Methods, Devices, And Systems For Non-Invasive Delivery Of Microwave Therapy"; and PCT Application Serial No. PCT/US08/60940, filed Apr. 18, 2008, and entitled "Systems And Methods For Creating An Effect Using Microwave Energy To Specified Tissue"; and PCT Application Serial No. PCT/US08/60922, filed Apr. 18, 2008, and entitled "Systems And Methods For Creating An Effect Using Microwave Energy To Specified Tissue." All of the above priority applications are expressly incorporated by reference in their entirety.

FIELD OF THE INVENTION

The present application relates to methods, apparatuses and systems for non-invasive delivery of energy, including microwave therapy. In particular, the present application relates to methods, apparatuses and systems for non-invasively delivering energy, such as, for example, microwave energy, to the epidermal, dermal and sub-dermal tissue of a patient to achieve various therapeutic and/or aesthetic results.

DESCRIPTION OF THE RELATED ART

It is known that energy-based therapies can be applied to tissue throughout the body to achieve numerous therapeutic and/or aesthetic results. There remains a continual need to improve on the effectiveness of these energy-based therapies and provide enhanced therapeutic results with minimal adverse side effects or discomfort.

BRIEF DESCRIPTION OF THE DRAWINGS

The invention will be understood from the following detailed description of preferred embodiments, taken in conjunction with the accompanying drawings, wherein.

DESCRIPTION OF THE PREFERRED EMBODIMENT

Although the disclosure hereof is detailed and exact to enable those skilled in the art to practice the invention the physical embodiments herein disclosed merely exemplify the invention which may be embodied in other specific structures. While the preferred embodiment has been described, the details may be changed without departing from the invention which is defined by the claims.

Figure 1:
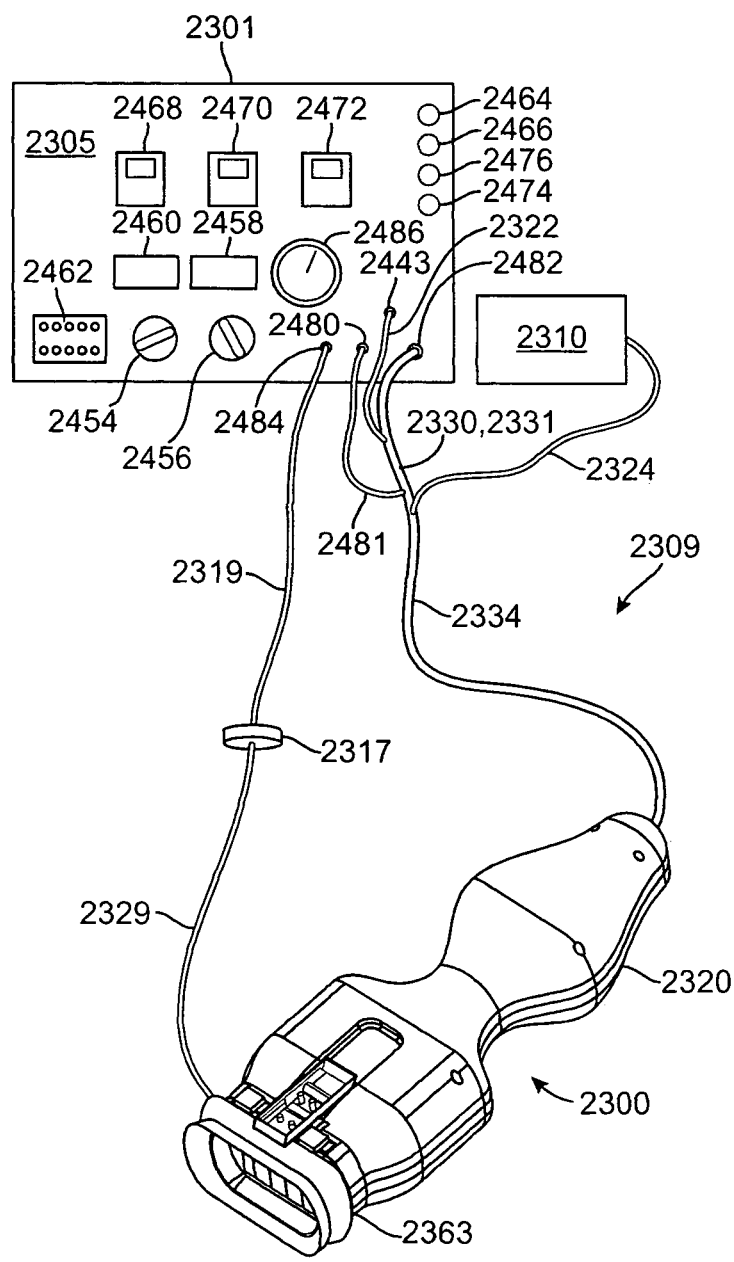
FIG. 1 is an illustration of a system including a generator, applicator and disposable according to an embodiment of the invention.

FIG. 1 is an illustration of a system 2309 including a generator 2301, applicator 2320 (which may also be referred to as re-usable) and disposable 2363 according to an embodiment of the invention. According to an embodiment of the invention applicator 2320 and disposable 2363 may comprise a medical treatment device 2300. According to an embodiment of the invention generator 2301 may operate in the ISM band of 5.775 to 5.825 GHz. According to an embodiment of the invention generator 2301 may have a Frequency centered at approximately 5.8 GHz. According to an embodiment of the invention generator 2301 includes circuitry for setting and controlling output power; measuring forward and reverse power and setting alarms. According to an embodiment of the invention generator 2301 may have a power output of between approximately 40 Watts and approximately 100 Watts. According to an embodiment of the invention generator 2301 may have a power output of between approximately 40 Watts and approximately 100 Watts where said output is measured into a 50 ohm load. According to an embodiment of the invention generator 2301 may have a power output of approximately 55 Watts measured into a 50 ohm load. According to an embodiment of the invention disposable 2363 and applicator 2320 may be formed into two separable units. According to an embodiment of the invention disposable 2363 and applicator 2320 may be formed into a single unit. According to an embodiment of the invention when combined disposable 2363 and applicator 2320 may form a medical treatment device 2300. According to an embodiment of the invention generator 2301 may be a microwave generator. According to an embodiment of the invention in system 2309 applicator 2320 may be connected to generator 2301 by applicator cable 2334. According to an embodiment of the invention in system 2309 applicator cable 2334 may include coolant conduit 2324, energy cable 2322, coolant thermocouple wires 2331, cooling plate thermocouple wires 2330 and antenna switch signal 2481. According to an embodiment of the invention in system 2309 coolant conduit 2324 may be connected to a coolant source 2310 (which may be, for example, a Nanotherm industrial recirculation chiller with 8 pounds per square inch pump output pressure available from ThermoTek, Inc). According to an embodiment of the invention in system 2309 energy cable 2322 may be connected to generator 2301 by microwave output connector 2443. According to an embodiment of the invention in system 2309 antenna switch signal 2481 may be connected to generator 2301 by antenna switch connector 2480. According to an embodiment of the invention in system 2309 disposable 2363 may be connected to generator 2301 by vacuum tubing 2319 which may include generator bio-barrier 2317, which may be, for example, a hydrophobic filter. According to an embodiment of the invention in system 2309 vacuum tubing 2319 may be connected to generator 2301 by vacuum port connector 2484. According to an embodiment of the invention in system 2309 front panel 2305 of generator 2301 may include power control knob 2454, vacuum control knob 2456, antenna select switch 2462 (which may include both display elements and selection switches), vacuum meter 2486, antenna temperature display 2458, coolant temperature display 2460, pre-cool timer 2468 (which may include both display elements and time set elements), energy timer 2470 (which may include both display elements and time set elements), post-cool timer 2472 (which may include both display elements and time set elements), start button 2464, stop button 2466, ready indicator 2476 and fault indicator 2474. According to an embodiment of the invention an error signal is sent to generator 2301 if a measured signal is outside of the specification for the requested power set by the power control knob 2454 on front panel 2305. According to an embodiment of the invention vacuum tube 2319 may include a flexible vacuum hose 2329 and a generator bio-barrier 2317. According to an embodiment of the invention flexible vacuum hose 2329 is adapted to collect fluids, such as, for example sweat or blood, which may escape disposable 2363 so that such fluids do not reach generator 2301. According to an embodiment of the invention generator bio-barrier 2317 may include a hydrophobic filter to keep fluids out of vacuum port connector 2484 of generator 2301. According to an embodiment of the invention generator bio-barrier 2317 may include a hydrophobic filter, such as, for example, a Millex FH Filter made of 0.45 micrometer hydrophobic PTFE which is available from Milipore. According to an embodiment of the invention generator bio-barrier 2317 may be positioned in vacuum tube 2319 between flexible vacuum hose 2329 and vacuum port connector 2484. According to an embodiment of the invention applicator cable 2334 may connect generator 2301 to applicator 2320. According to an embodiment of the invention cooling plate thermocouple wires 2330 and coolant thermocouple wires 2331 may be connected to generator 2301 by temperature connector 2482. According to an embodiment of the invention coolant conduit 2324 may convey cooling fluid from a coolant source 2310 to applicator 2320. According to an embodiment of the invention applicator cable 2334 may convey microwave switch selection data to applicator 2320 and temperature data from thermocouples in applicator 2320 to generator 2301. According to an embodiment of the invention applicator cable 2334 may comprise one or more separate cables and connectors. According to an embodiment of the invention a generator connector may be designed and adapted to connect applicator cable 2334 to generator 2301, including connections for cooling conduit 2324, antenna switch signal 2481, energy cable 2322, cooling plate thermocouple wires 2330 and coolant thermocouple wires 2331.

Figure 2:
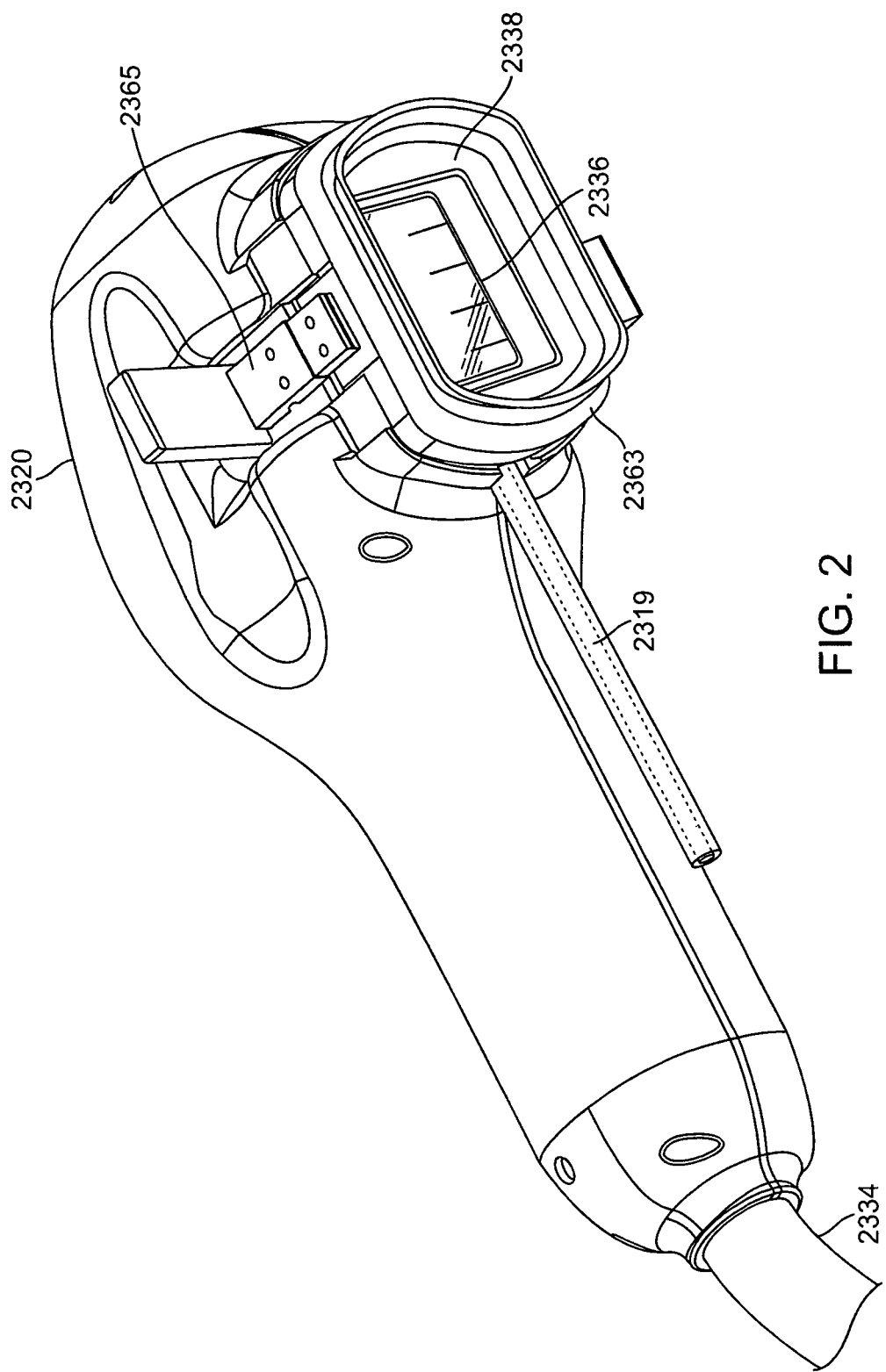
FIG. 2 is a perspective view of a medical treatment device, including an applicator and disposable, according to an embodiment of the invention.

FIG. 2 is a perspective view of a medical treatment device 2300 including an applicator 2320 and disposable 2363 according to an embodiment of the invention. According to an embodiment of the invention applicator 2320 may be attached to disposable 2363 by latching mechanism 2365. According to an embodiment of the invention applicator 2320 may include applicator cable 2334. According to an embodiment of the invention disposable 2363 may include vacuum tubing 2319, tissue chamber 2338 and tissue interface surface 2336.

Figure 3:
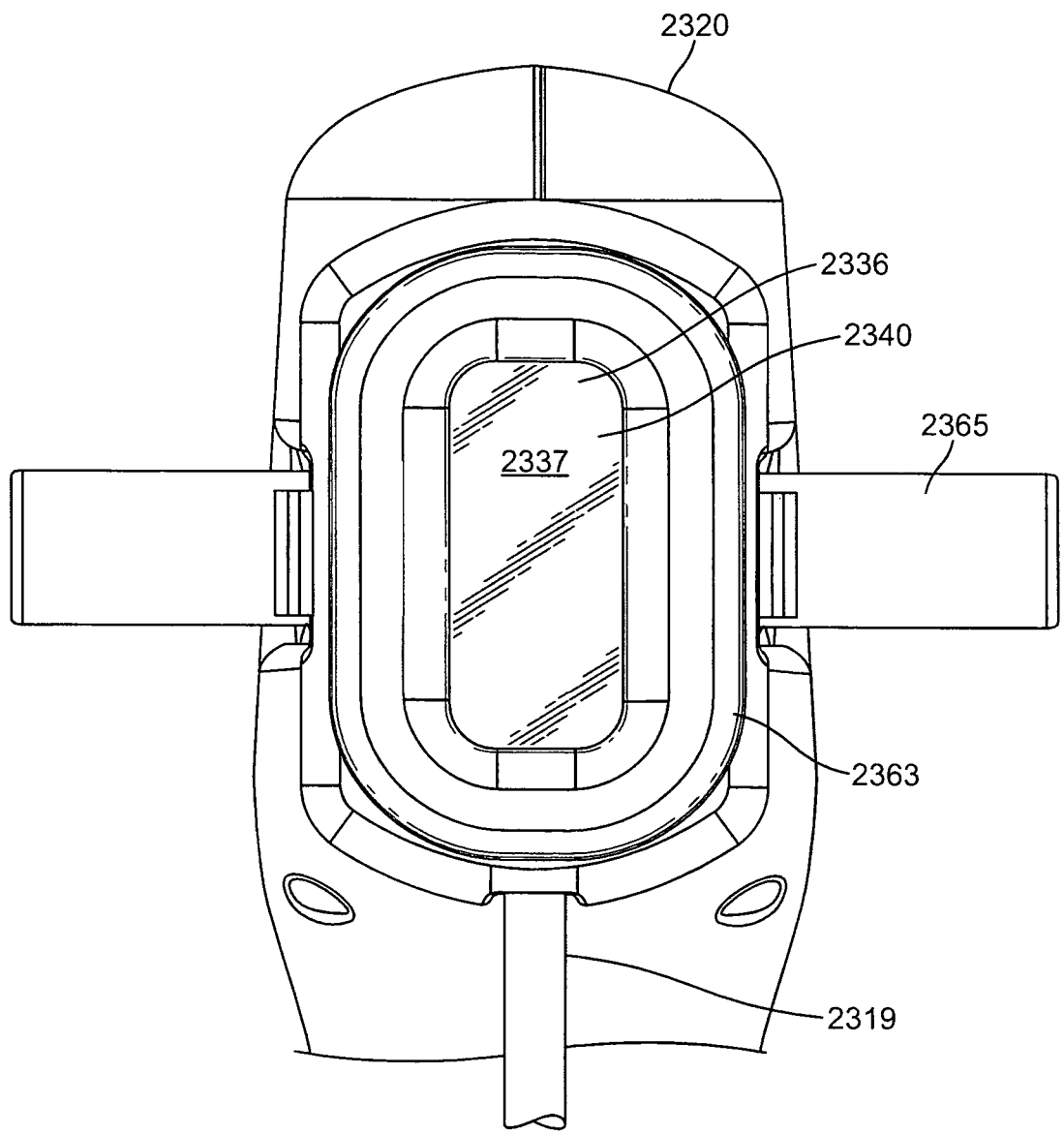
FIG. 3 is an end on view of the distal end of a medical treatment device, including an applicator and the disposable according to an embodiment of the invention.

FIG. 3 is an end on view of a distal end of a medical treatment device 2300 including an applicator 2320 and disposable 2363 according to an embodiment of the invention. According to an embodiment of the invention disposable 2363 may include tissue bio-barrier 2337. According to an embodiment of the invention applicator 2320 may include cooling plate 2340, which may be, for example, positioned behind tissue bio-barrier 2337. According to an embodiment of the invention tissue bio-barrier 2337 may form a portion of tissue interface surface 2336. According to an embodiment of the invention latching mechanism 2365 may be used to facilitate the connection of disposable 2363 to applicator 2320.

Figure 4:
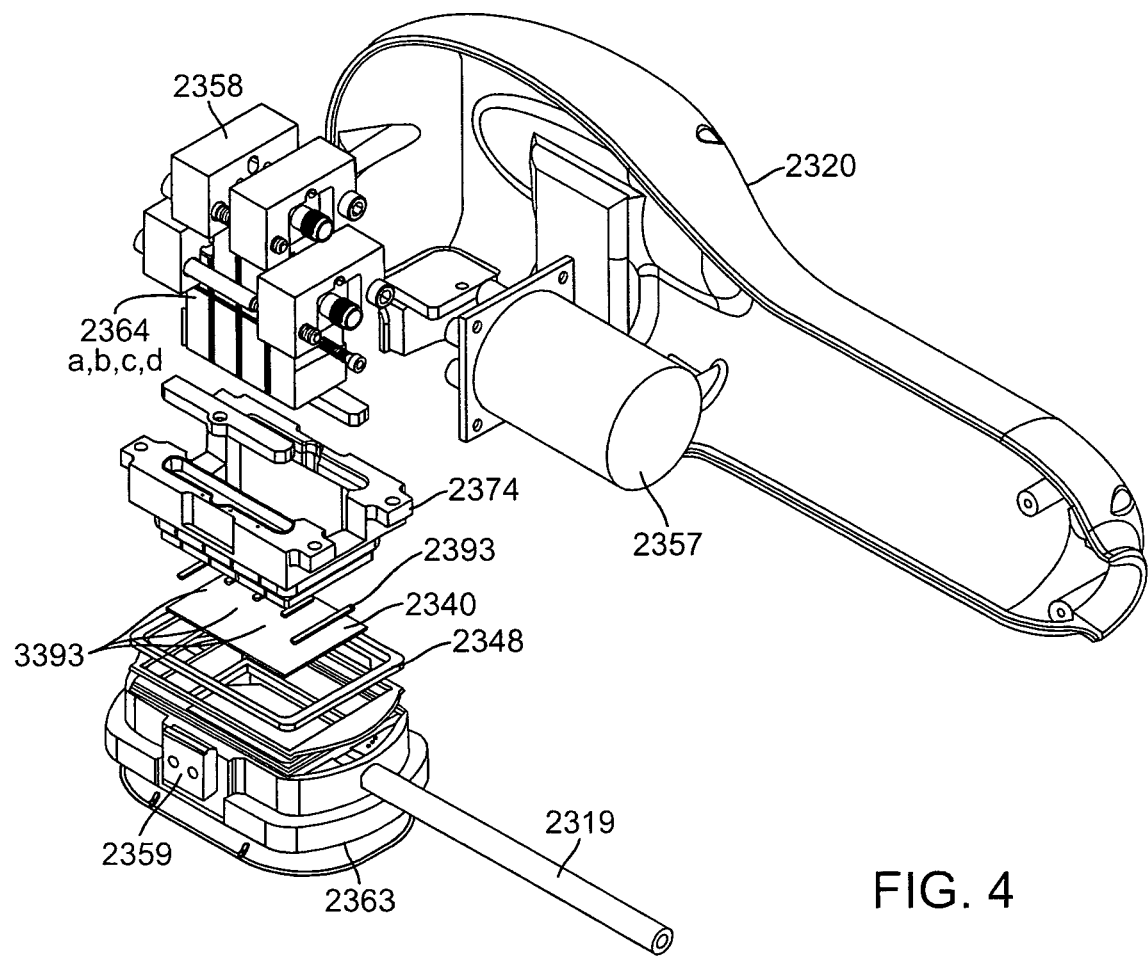
FIG. 4 is an exploded perspective view of a medical treatment device according to an embodiment of the invention.

FIG. 4 is a perspective view of a medical treatment device 2300 including an exploded perspective view of an applicator 2320 and a view of disposable 2363 according to the present invention. According to an embodiment of the invention applicator 2320 may include a cooling plate 2340, separation ribs 2393, intermediate scattering elements 3393, antenna cradle 2374, waveguide assembly 2358 and antenna switch 2357. According to an embodiment of the invention waveguide assembly 2358 may include antennas 2364(a-d). According to an embodiment of the invention disposable 2363 may include vacuum tubing 2319, latching elements 2359 and vacuum seal 2348.

Figure 5:
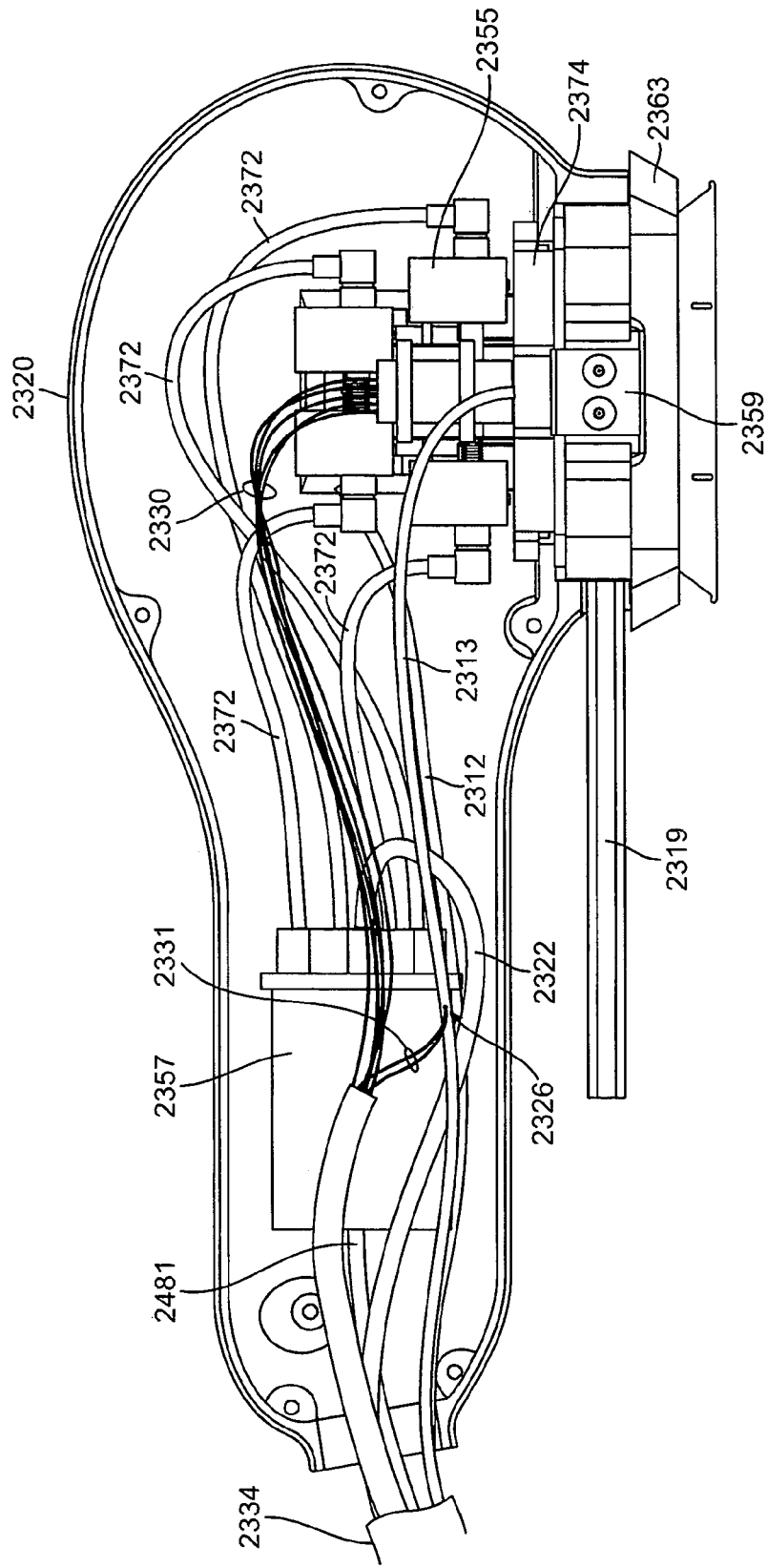
FIG. 5 is a view of a medical treatment device according to an embodiment of the invention including a cutaway view of applicator according to an embodiment of the invention.

FIG. 5 is a view of a medical treatment device 2300 according to an embodiment of the present invention including a cutaway view of applicator 2320 and disposable 2363. According to an embodiment of the invention applicator 2320 may include antenna array 2355, antenna switch 2357 and applicator cable 2334. According to an embodiment of the invention applicator cable 2334 may include cooling plate thermocouple wires 2330, coolant thermocouple wires 2331, coolant supply tubing 2312, coolant return tubing 2313, antenna switch signal 2481, energy cable 2322. According to an embodiment of the invention cooling plate thermocouple wires 2330 may include one or more thermocouple wires which may be attached to an or more thermocouples positioned opposite an output of antenna array 2355. According to an embodiment of the invention coolant thermocouple wires 2331 may include one or more thermocouple wires attached to an or more cooling path thermocouples 2326 which may be positioned to measure coolant fluid, such as, for example, in coolant return tubing 2313. According to an embodiment of the invention one or more cooling path thermocouples 2326 may be positioned to measure the temperature of cooling fluid 2361 after it passes through coolant chamber 2360. According to an embodiment of the invention one or more cooling path thermocouples 2326 may be located in coolant return tubing 2313. According to an embodiment of the invention cooling path thermocouples 2326 may function to provide feedback to generator 2301 indicative of the temperature of cooling fluid 2361 after cooling fluid 2361 passes through coolant chamber 2360. According to an embodiment of the invention disposable 2363 may include latching element 2359. According to an embodiment of the invention applicator cable 2334 may include interconnect cables 2372 to transmit signals to antenna array 2355. According to an embodiment of the invention antenna array 2355 may include antenna cradle 2374.

Figure 6:
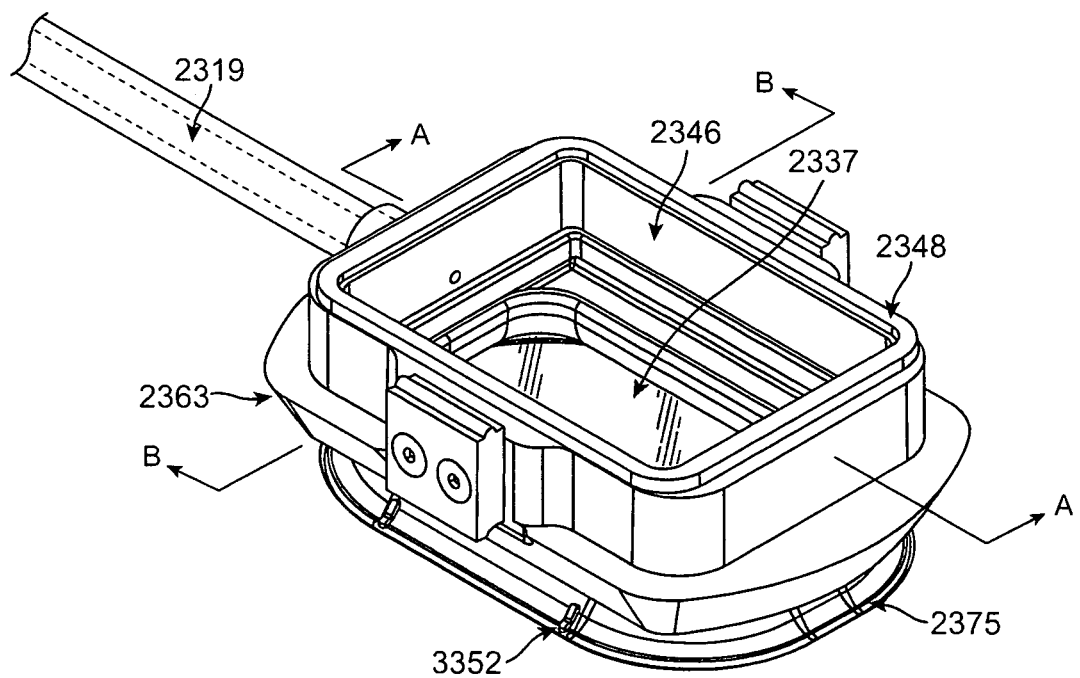
FIG. 6 is a perspective view of a disposable according to an embodiment of the invention.
Figure 7:
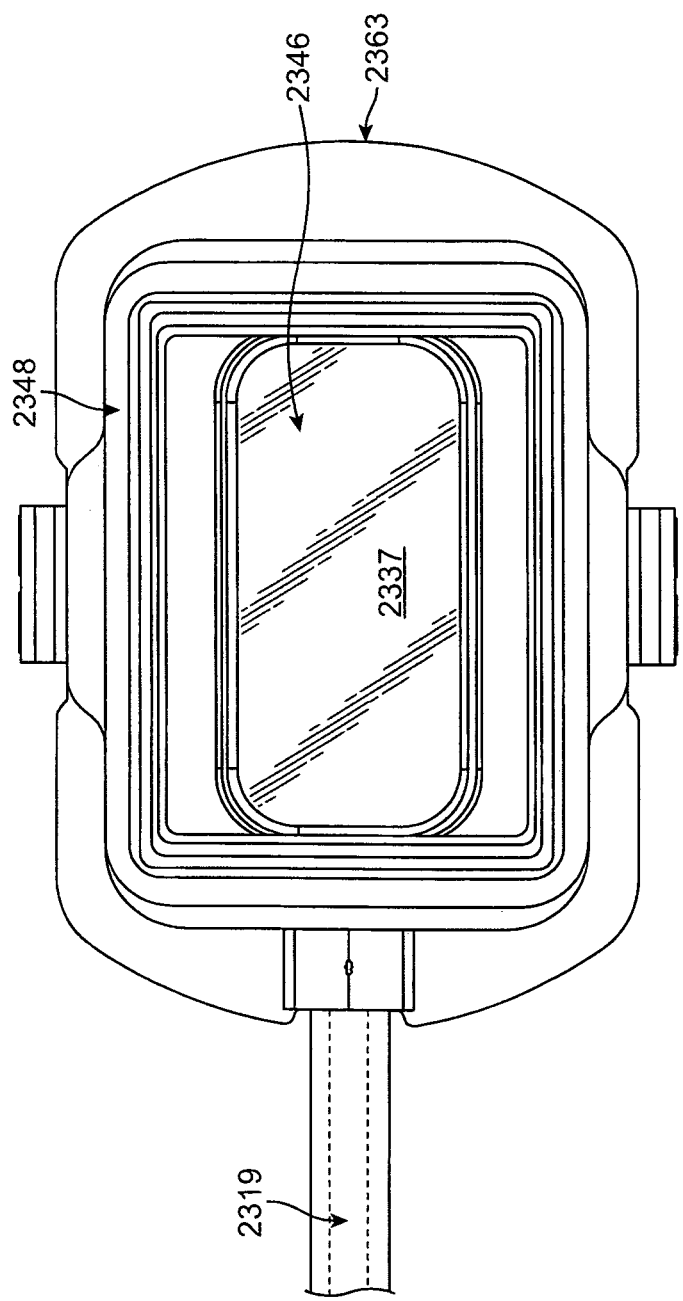
FIG. 7 is a view of a proximal side of a disposable according to an embodiment of the invention.
Figure 8:
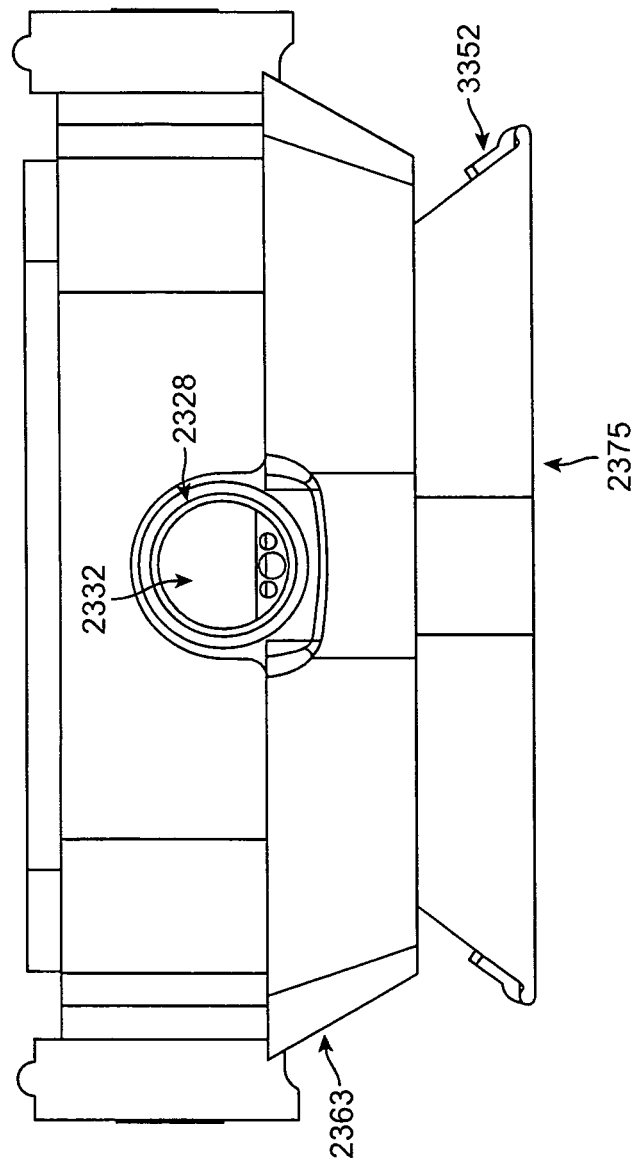
FIG. 8 is a side view of one end of a disposable according to an embodiment of the invention.
Figure 9:
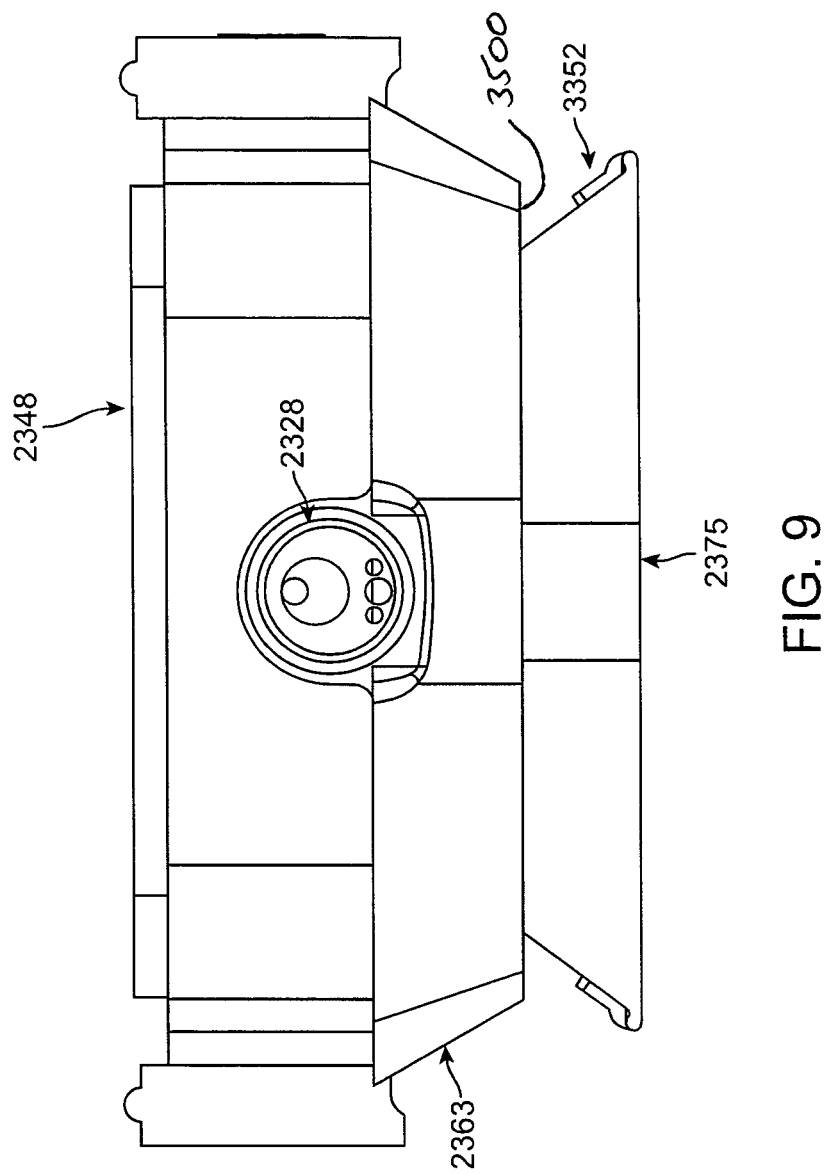
FIG. 9 is a side view of one end of a disposable according to an embodiment of the invention.
Figure 10:
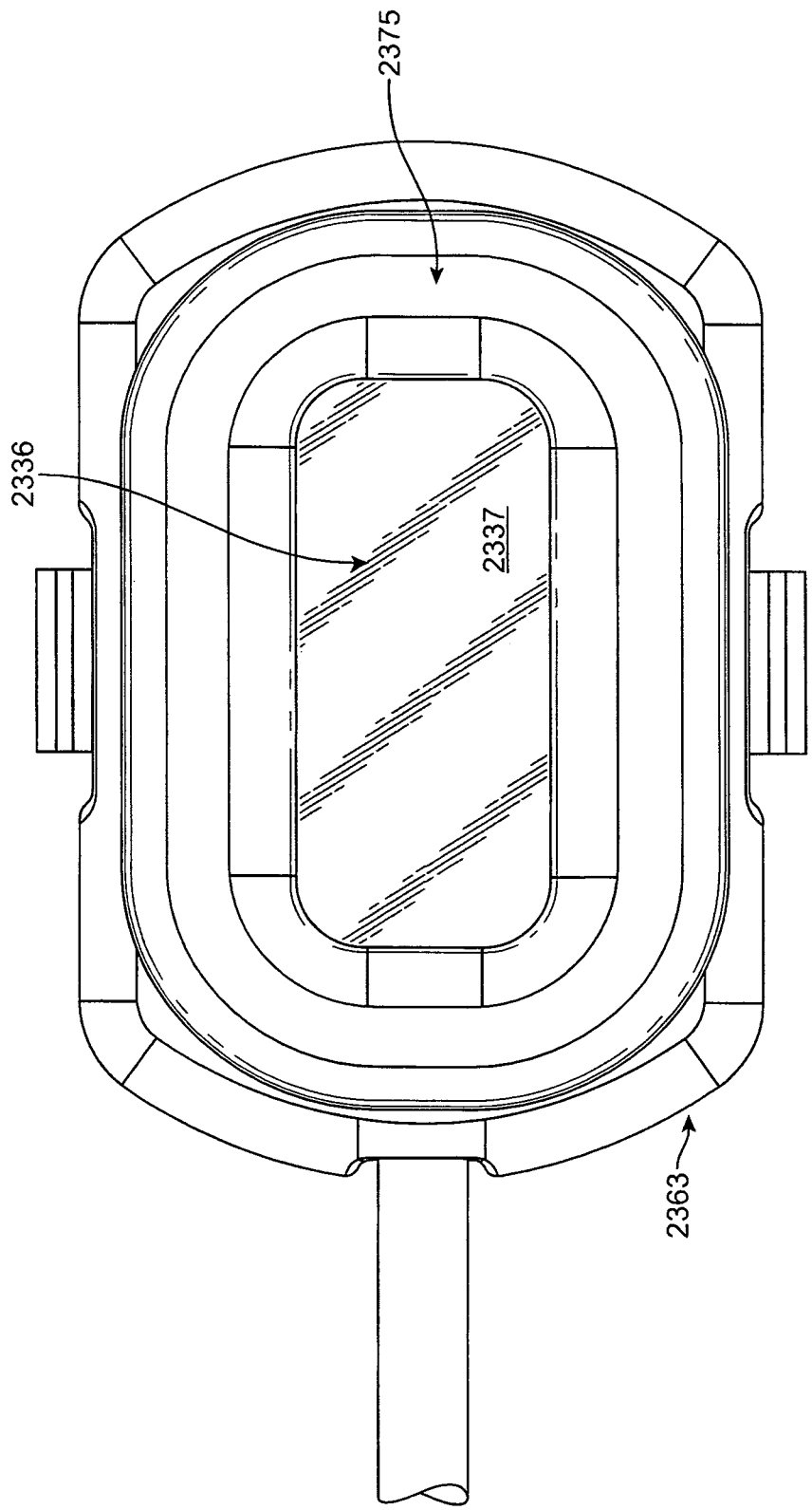
FIG. 10 is a view of a distal side of a disposable according to an embodiment of the invention.
Figure 11:
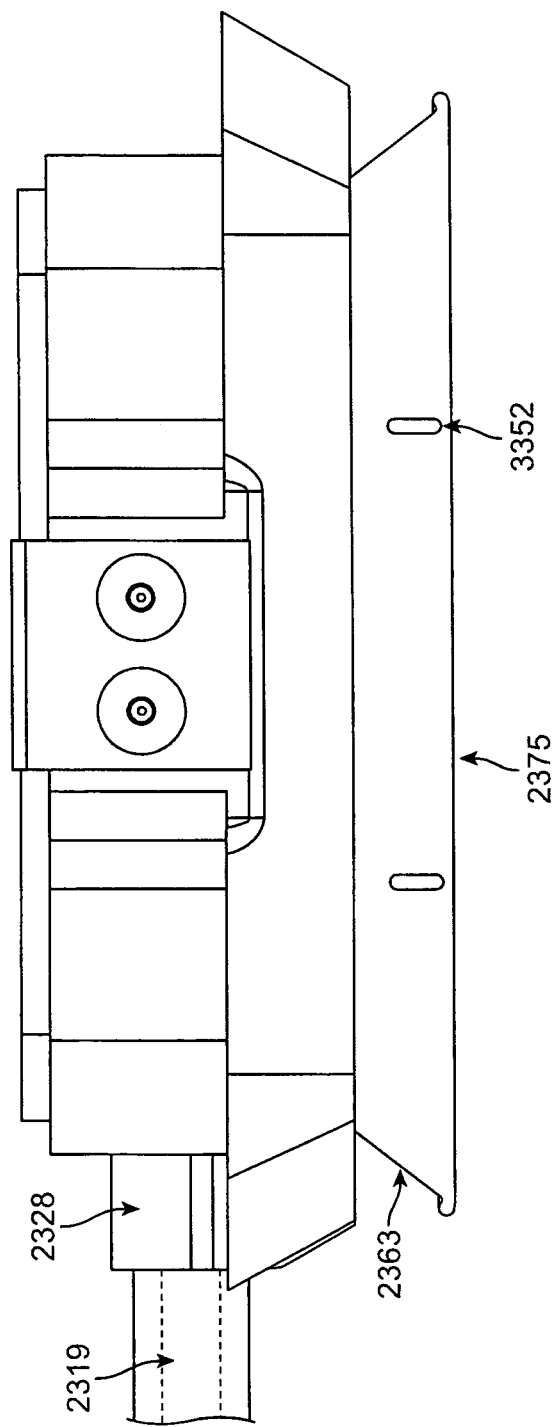
FIG. 11 is a side view of a disposable according to an embodiment of the invention.
Figure 12:
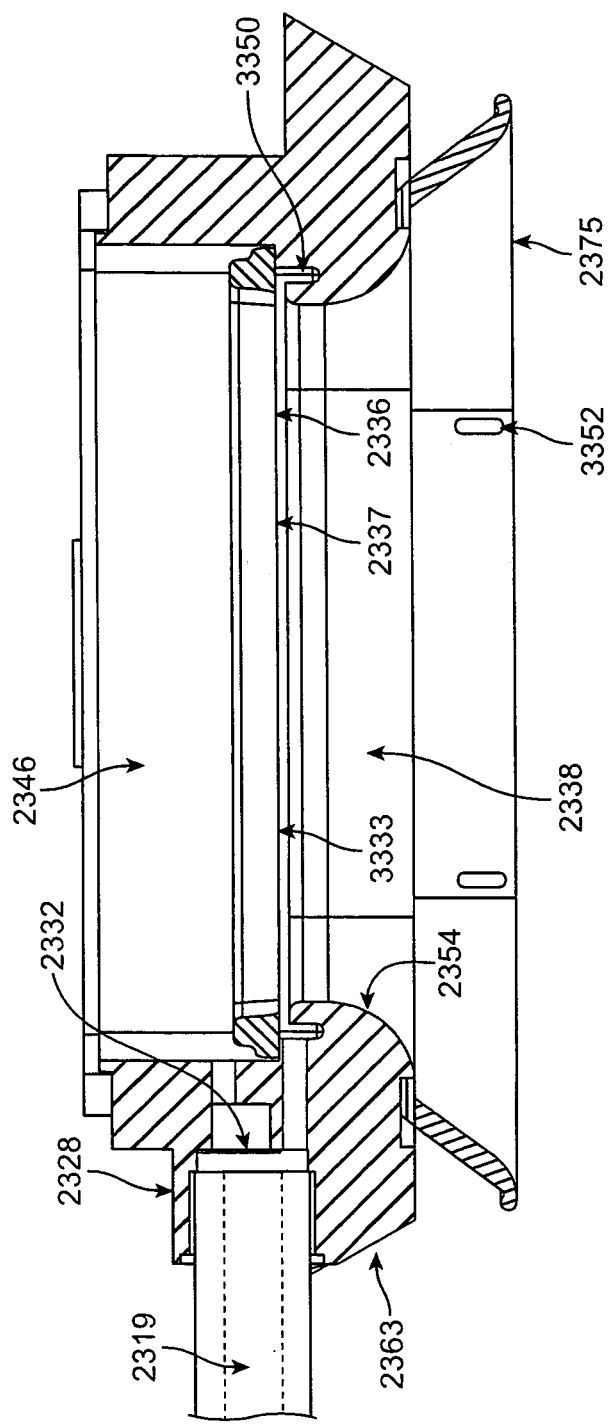
FIG. 12 is a cutaway side view of a disposable according to an embodiment of the invention.
Figure 13:
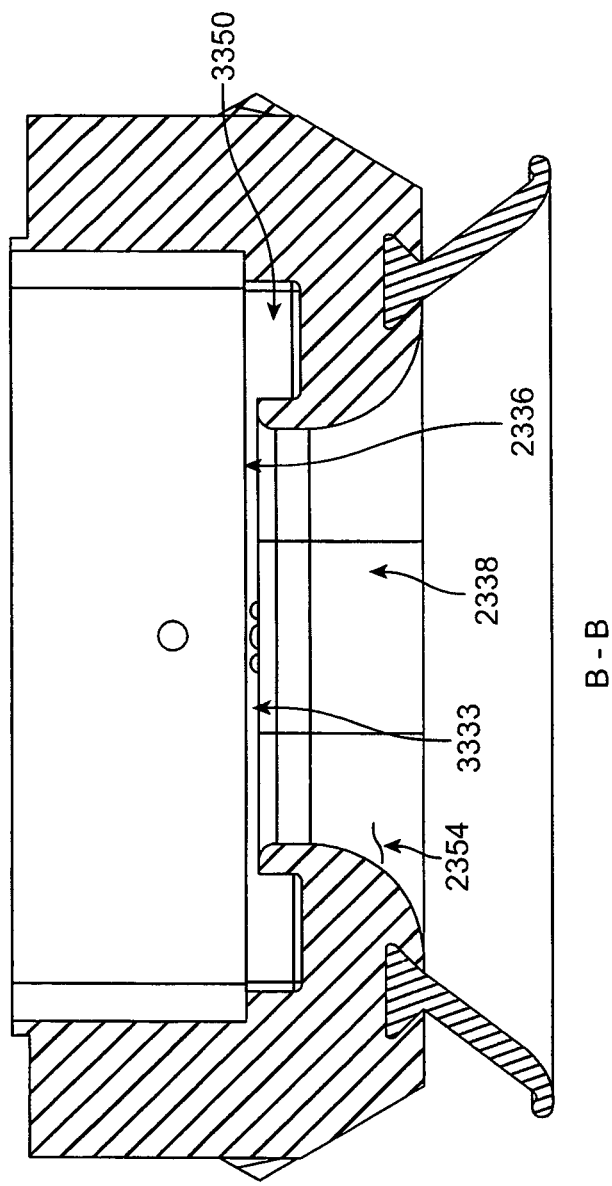
FIG. 13 is a cutaway side view of a disposable according to an embodiment of the invention.
Figure 14:
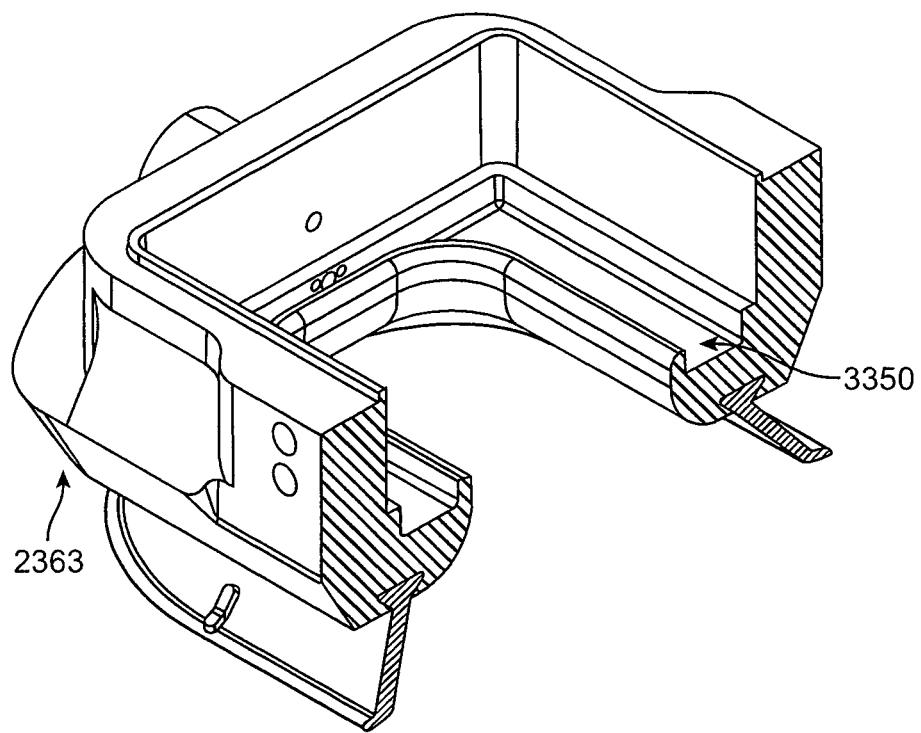
FIG. 14 is a cutaway perspective view of a disposable according to an embodiment of the invention.
Figure 15:
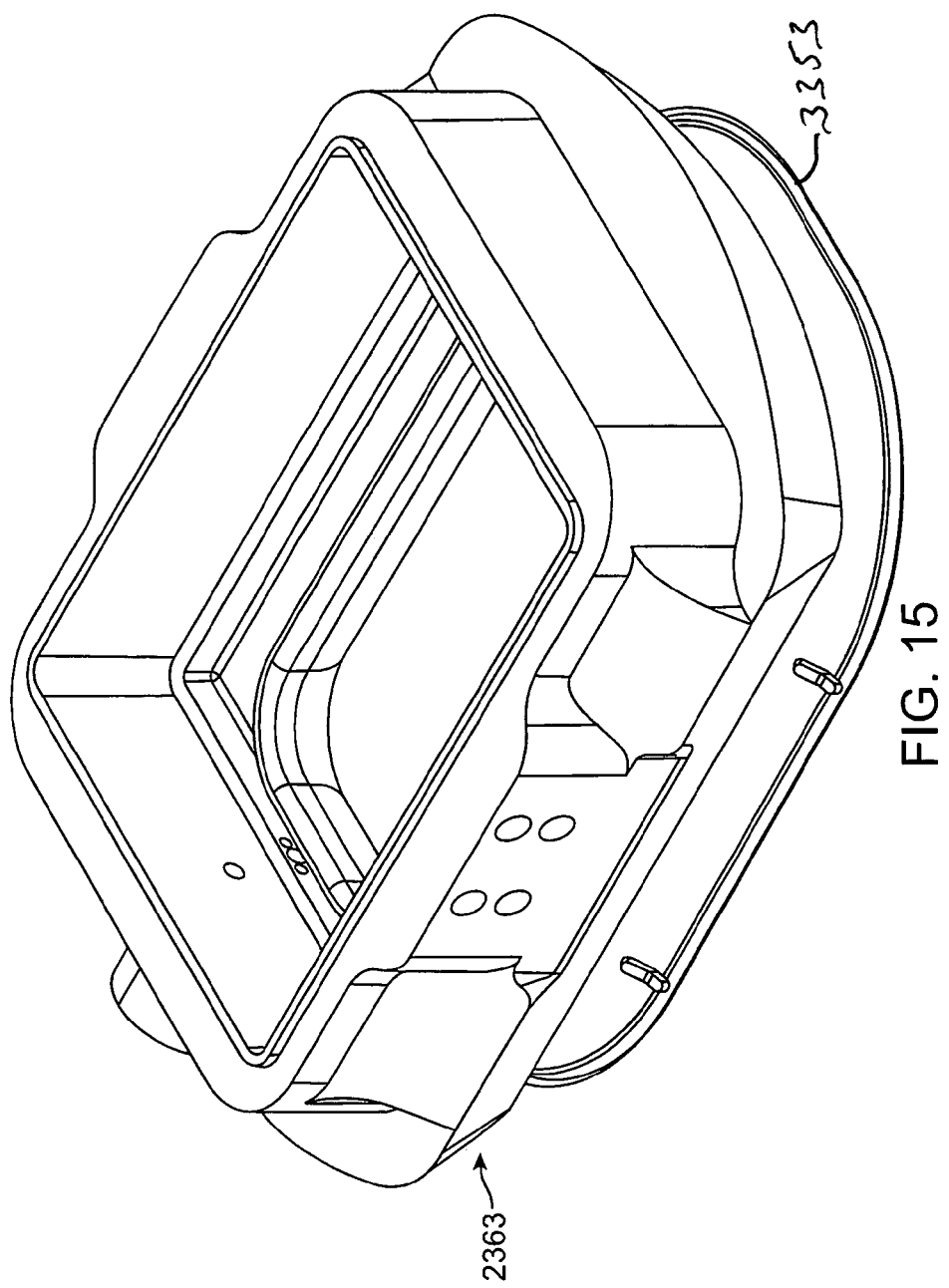
FIG. 15 is a top perspective view of a proximal end of a disposable according to an embodiment of the invention.

FIG. 6 is a perspective view of disposable 2363 according to an embodiment of the invention. FIG. 7 is a view of the proximal side of disposable 2363 according to an embodiment of the invention. FIG. 8 is a side view of one end of disposable 2363 according to an embodiment of the invention. FIG. 9 is a side view of one end of disposable 2363 according to an embodiment of the invention. FIG. 10 is a view of the distal side of disposable 2363 according to an embodiment of the invention. FIG. 11 is a side view of disposable 2363 according to an embodiment of the invention. FIG. 12 is a cutaway side view of disposable 2363 according to an embodiment of the invention. FIG. 13 is a cutaway side view of disposable 2363 according to an embodiment of the invention. FIG. 14 is a cutaway perspective view of disposable 2363 according to an embodiment of the invention. FIG. 15 is a top perspective view of a proximal end of disposable 2363 according to an embodiment of the invention.

According to an embodiment of the invention disposable 2363 may include tissue interface surface 2336, tissue chamber 2338 and alignment features 3352. According to an embodiment of the invention tissue interface surface 2336 may form a back wall of tissue chamber 2338. According to an embodiment of the invention tissue interface surface 2336 may include tissue bio-barrier 2337 and vacuum passage 3333. According to an embodiment of the invention vacuum passage 3333 may also be referred to as a lip or rim. According to an embodiment of the invention disposable 2363 may include alignment features 3352 and vacuum tubing 2319. According to an embodiment of the invention disposable 2363 may include compliant member 2375. According to an embodiment of the invention chamber walls 2354 may include a compliant member 2375. According to an embodiment of the invention compliant member 2375 may be formed from a compliant material, such as, for example, rubber, coated urethane foam (with a compliant plastic or rubber seal coating), silicone, polyurethane or heat sealed open cell foam. According to an embodiment of the invention compliant member 2375 may be positioned around the outer edge of tissue chamber 2338 to facilitate the acquisition of tissue. According to an embodiment of the invention compliant member 2375 may be positioned around the outer edge of chamber opening 2339 to facilitate the acquisition of tissue. According to an embodiment of the invention compliant member 2375 may facilitate the engagement of tissue which is not flat, such as, for example tissue in the axilla. According to an embodiment of the invention compliant member 2375 may facilitate the engagement of tissue which is not flat, such as, for example tissue in the outer regions of the axilla. According to an embodiment of the invention compliant member 2375 may provide improved sealing characteristics between the skin and tissue chamber 2338, particularly where the skin is not flat. According to an embodiment of the invention compliant member 2375 may speed the acquisition of tissue in tissue chamber 2338, particularly where the skin is not flat. According to an embodiment of the invention compliant member 2375 may have a height of between approximately 0.15 inches and approximately 0.40 inches above chamber opening 2339 when compliant member 2375 is not compressed. According to an embodiment of the invention compliant member 2375 may have a height of approximately 0.25 inches above chamber opening 2339 when compliant member 2375 is not compressed. According to an embodiment of the invention alignment features 3352 may be positioned at a distance which facilitate appropriate placement of applicator 2320 during treatment. According to an embodiment of the invention alignment features 3352 may be positioned approximately 30.7 millimeters apart. According to an embodiment of the invention alignment features 3352 may be further positioned and may be designed to assist a physician in positioning applicator 2320 prior to the application of energy. According to an embodiment of the invention alignment features 3352 on disposable 2363 assist the user in properly positioning the applicator prior to treatment and in moving the applicator to the next treatment region during a procedure. According to an embodiment of the invention alignment features 3352 on disposable 2363, when used with marks or landmarks in a treatment region facilitate the creation of a continuous lesion. According to an embodiment of the invention alignment features 3352 may be used to align medical treatment device 2300 before suction is applied. According to an embodiment of the invention an outer edge of compliant member 2375 may assist a user in aligning medical treatment device 2300.

According to an embodiment of the invention compliant member 2375, which may also be referred to as a skirt or flexible skirt, may be manufactured from silicone. According to an embodiment of the invention compliant member 2375 may extend approximately 0.25" from rigid surface 3500.

According to an embodiment of the invention a counter sink or dovetail notch 2356 may be positioned in rigid disposable surface 3500 around the outer edge of chamber opening 2339 to assist in alignment of compliant member 2375. According to an embodiment of the invention the compliant member 2375 may have a durometer density rating (softness) of approximately A60 which may help compliant member 2375 to maintain its shape better while being easier to mold. According to an embodiment of the invention colorant may be used in compliant member 2375 to contrast with skin viewed through compliant member 2375, making it easier for user, such as a physician to distinguish between skin and a distal surface of compliant member 2375. According to an embodiment of the invention colorant may be used in compliant member 2375 to make it easier for user, such as a physician to distinguish between skin and an outer edge of compliant member 2375. According to an embodiment of the invention colorant may be used in compliant member 2375 to help a user distinguish an edge of compliant member 2375 from surrounding skin and assist in aligning of medical treatment device 2300. According to an embodiment of the invention the angle of compliant member 2375 relative to rigid surface 3500 may be approximately 53 degrees when compliant member 2375 is not compressed.

According to an embodiment of the invention disposable 2363 includes applicator chamber 2346. According to an embodiment of the invention disposable 2363 may include an applicator chamber 2346 which may be formed, at least in part, by tissue bio-barrier 2337. According to an embodiment of the invention disposable 2363 may include applicator bio-barrier 2332 (which may be, for example, a polyethylene film, available from Fisher Scientific), and vacuum passage 3333. According to an embodiment of the invention a counter bore may positioned between applicator bio-barrier 2332 and applicator chamber 2346.

According to an embodiment of the invention vacuum passage 3333 connects vacuum channel 3350 to tissue chamber 2338. According to an embodiment of the invention vacuum channel 3350 may also be referred to as a reservoir or vacuum reservoir. According to an embodiment of the invention vacuum connector 2328 is connected to vacuum passage 3333 through vacuum channel 3350. According to an embodiment of the invention vacuum channel 3350 may connect vacuum passages 3333 connect vacuum connector 2328 in tissue chamber 2338. According to an embodiment of the invention vacuum passages 3333 form a direct path to tissue interface surface 2336. According to an embodiment of the invention vacuum passages 3333 and vacuum channel 3350 may be adapted to restrict the movement of fluids from tissue chamber 2338 to applicator bio-barrier 2332. According to an embodiment of the invention vacuum connector 2328 may be positioned on the same side of disposable 2363 as applicator bio-barrier 2332. According to an embodiment of the invention applicator bio-barrier 2332 may be designed to prevent fluids from tissue chamber 2338 from reaching applicator chamber 2346, particularly when there is back pressure caused by, for example, a vacuum created in tissue chamber 2338 as tissue is pulled away from tissue interface surface 2336. According to an embodiment of the invention vacuum pressure may be used to support tissue acquisition in tissue chamber 2338. According to an embodiment of the invention vacuum pressure may be used to pull tissue into tissue chamber 2338. According to an embodiment of the invention vacuum pressure may be used to maintain tissue in tissue chamber 2338. According to an embodiment of the invention vacuum channel 2350 may surround tissue interface surface 2336. According to an embodiment of the invention applicator bio-barrier 2332 may be positioned between vacuum passages 3333 and applicator chamber 2346. According to an embodiment of the invention applicator bio-barrier 2332 may be a membrane which may be adapted to be permeable to air but substantially impermeable to biological fluids such as, for example, blood and sweat. According to an embodiment of the invention applicator bio-barrier 2332 may be a hydrophobic membrane filter. According to an embodiment of the invention applicator bio-barrier 2332 may be made of polyethylene film, nylon or other suitable materials. According to an embodiment of the invention applicator bio-barrier 2332 may include pores having sizes sufficient to pass enough air to substantially equalize the vacuum pressure in applicator chamber 2346 and in tissue chamber 2338 without passing biological fluids from tissue chamber 2338 to applicator chamber 2346. According to an embodiment of the invention applicator bio-barrier 2332 may include pores having sizes of approximately 0.45 micrometers. According to an embodiment of the invention when the vacuum is turned on, and before pressure is equalized, applicator bio-barrier 2332 may induce a minimal pressure drop between vacuum passages 3333 and the applicator chamber 2346. According to an embodiment of the invention applicator chamber 2346 and tissue chamber 2338 may be separated, at least in part, by tissue bio-barrier 2337. According to an embodiment of the invention tissue chamber 2338 may include tissue interface surface 2336 and chamber wall 2354.

According to an embodiment of the invention tissue chamber opening 2339 has dimensions which facilitate the acquisition of tissue. According to an embodiment of the invention tissue chamber 2339 may be sized to facilitate tissue acquisition while being large enough to prevent interference with energy radiated from waveguide antennas 2364 in antenna array 2355 when applicator 2320 is attached to disposable 2363. According to an embodiment of the invention a vacuum circuit 3341 may include vacuum passages 3333, vacuum channel 3350 and may encircle tissue chamber 3338. According to an embodiment of the invention vacuum channel 3350 may be positioned around tissue chamber 2338. According to an embodiment of the invention vacuum passage 3333 may be positioned around a proximal end of tissue chamber 2338. According to an embodiment of the invention vacuum passage 3333 may be positioned around a proximal end of tissue chamber 2338 between tissue bio-barrier 2337 and a proximal end of chamber wall 2354. According to an embodiment of the invention an opening to vacuum passage 3333 may be approximately 0.020 inches in height. According to an embodiment of the invention an opening to vacuum passage 3333 may be approximately 0.010 inches in height when disposable 2363 is attached to applicator 2320 and tissue bio-barrier 2337 is stretched into tissue chamber 2338 by a distal end of applicator 2320. According to an embodiment of the invention vacuum passage 3333 may have an opening height which is too small for tissue to invade when a vacuum is applied.

According to an embodiment of the invention disposable 2363 may be manufactured from a clear or substantially clear material to assist a user, such as a physician in viewing tissue engagement. According to an embodiment of the invention the disposable 2363 may have an outer angle to allow a user to see alignment features 3352 on compliant member 2375 to assist a user in aligning medical treatment device 2300. According to an embodiment of the invention an angle around the outside of disposable 2363 provides a user with a direct view of alignment features 3352. According to an embodiment of the invention tissue chamber 2338 may have dimensions of approximately 1.54 inches by approximately 0.7 inches. According to an embodiment of the invention the 4 corners of tissue chamber 2338 may have a radius of 0.1875 inches. According to an embodiment of the invention antenna array 2335 may include four antennas and may have dimensions of approximately 1.34 inches by approximately 0.628 inches. According to an embodiment of the invention the dimensions of the waveguide array 2335 and tissue chamber 2338 may be optimized to minimizing stray fields forming at the edges of waveguide array 2335 as well as optimizing the effective cooling area of tissue interface surface 2336. According to an embodiment of the invention tissue chamber 2338 may be optimized to facilitate tissue acquisition without adversely impacting cooling or energy transmission.

Figure 16:
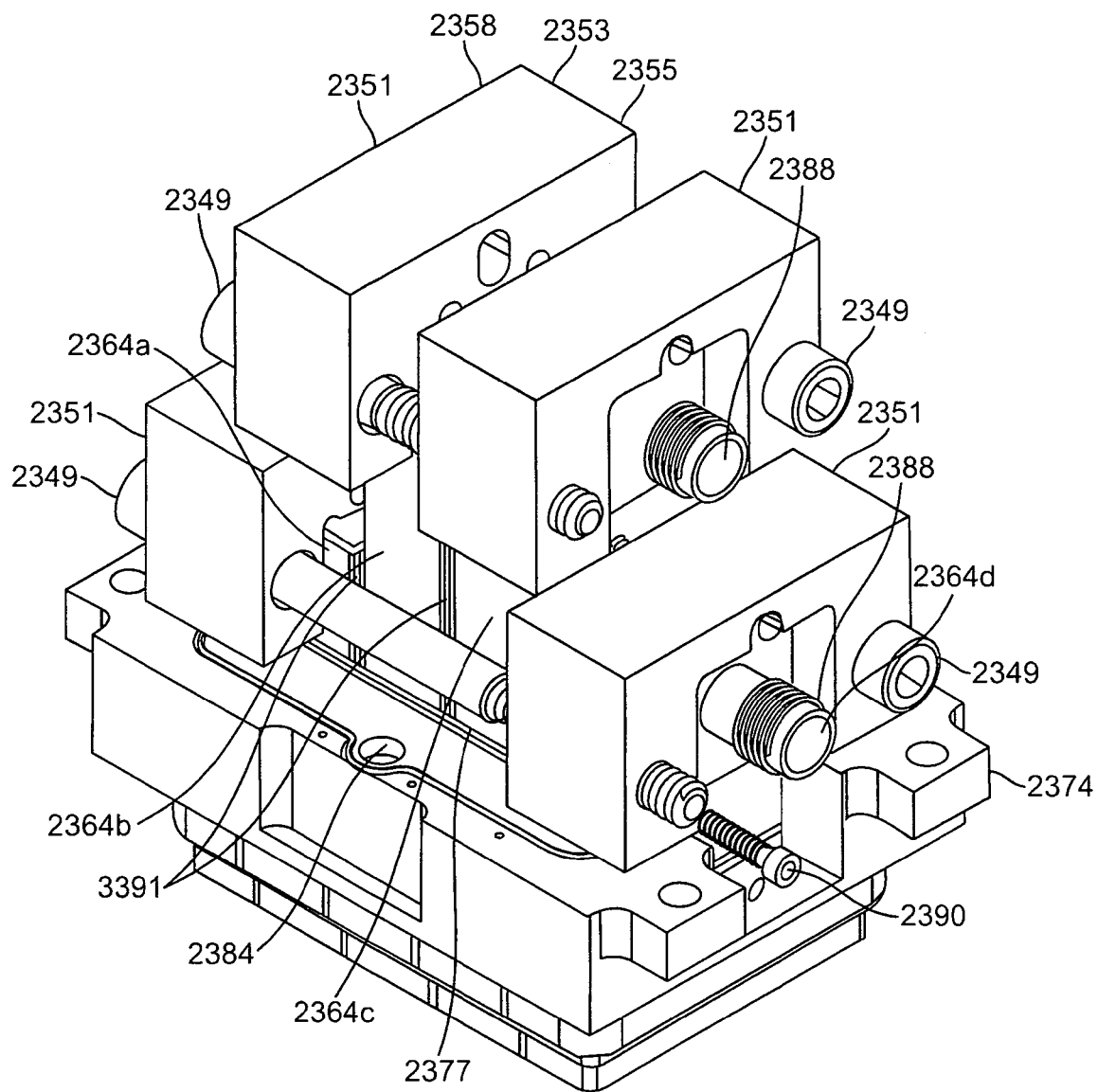
FIG. 16 is a perspective view of an antenna array according to an embodiment of the invention.

FIG. 16 is a perspective view of antenna array 2355 according to an embodiment of the invention. According to an embodiment of the invention antenna array 2355 may include antenna cradle 2374. According to an embodiment of the invention antenna cradle 2374 may include reservoir inlet 2384 and antenna chamber 2377. According to an embodiment of the invention waveguide assembly 2358 may include one or more spacer 3391 (which may be, for example, copper shims) positioned between waveguide antennas 2364. According to an embodiment of the invention spacer 3391 may be positioned between waveguide antenna 2364a and waveguide antenna 2364b. According to an embodiment of the invention spacer 3391 may be positioned between waveguide antenna 2364b and waveguide antenna 2364c. According to an embodiment of the invention spacer 3391 may be positioned between waveguide antenna 2364c and waveguide antenna 2364d. According to an embodiment of the invention microwave energy may be supplied to each waveguide antenna through feed connectors 2388. According to an embodiment of the invention waveguide assembly 2358 may be held together by a waveguide assembly frame 2353. According to an embodiment of the invention waveguide assembly frame 2353 may include feed brackets 2351 and assembly bolts 2349. According to an embodiment of the invention antenna array 2355 may include antenna cradle 2374 and least one waveguide antenna 2364. According to an embodiment of the invention antenna array 2355 may include one or more spacer 3391. According to an embodiment of the invention antenna array 2355 may include four waveguide antennas 2364a, 2364b, 2364c and 2364d. According to an embodiment of the invention the heights of waveguide antennas 2364 in antenna array 2355 may be staggered to facilitate access to feed connectors 2388. According to an embodiment of the invention one or more waveguide antenna 2364 in antenna array 2355 may include tuning element 2390.

Figure 17:
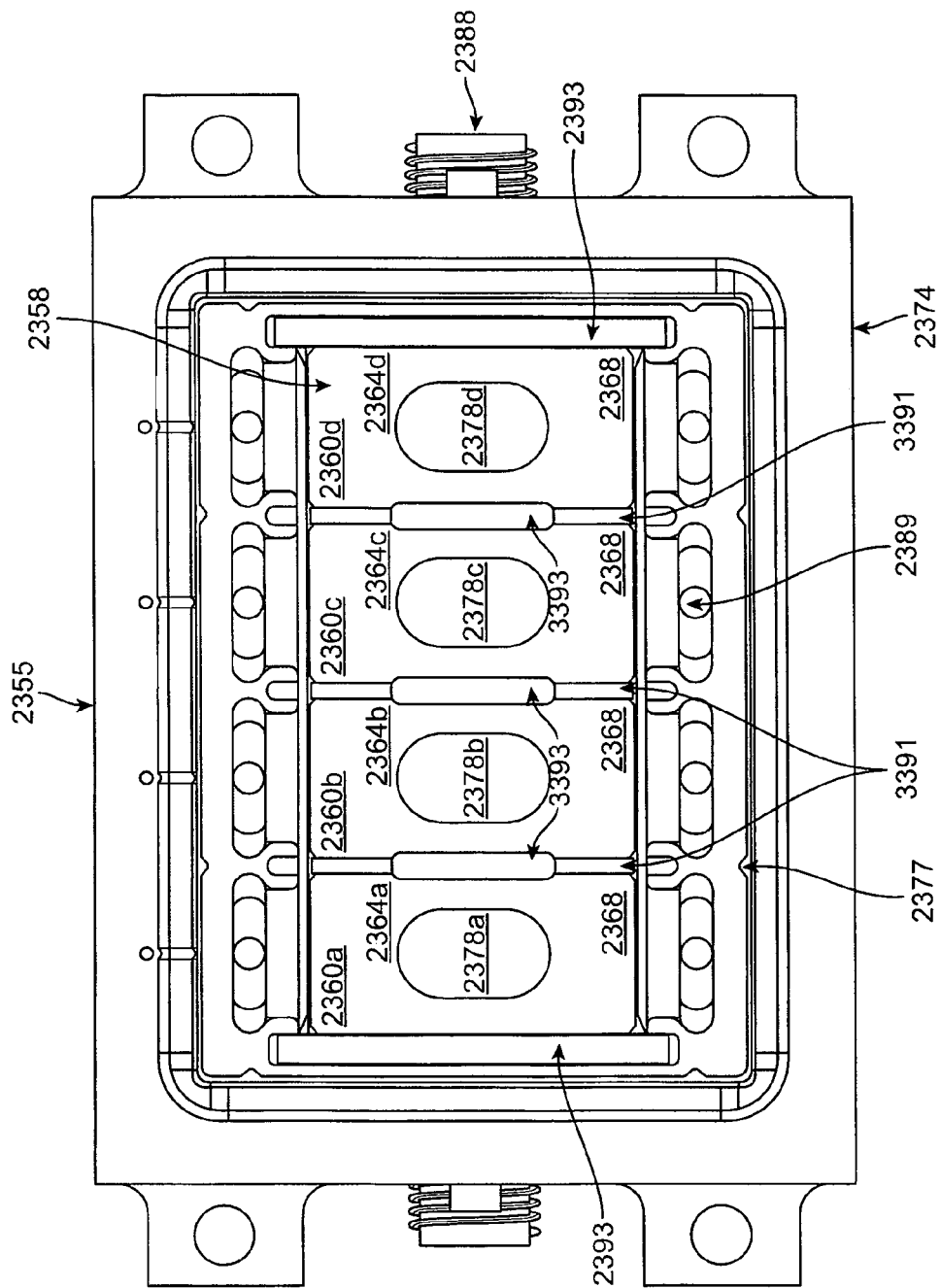
FIG. 17 is an end view of a portion of an antenna array according to an embodiment of the invention.
Figure 18:
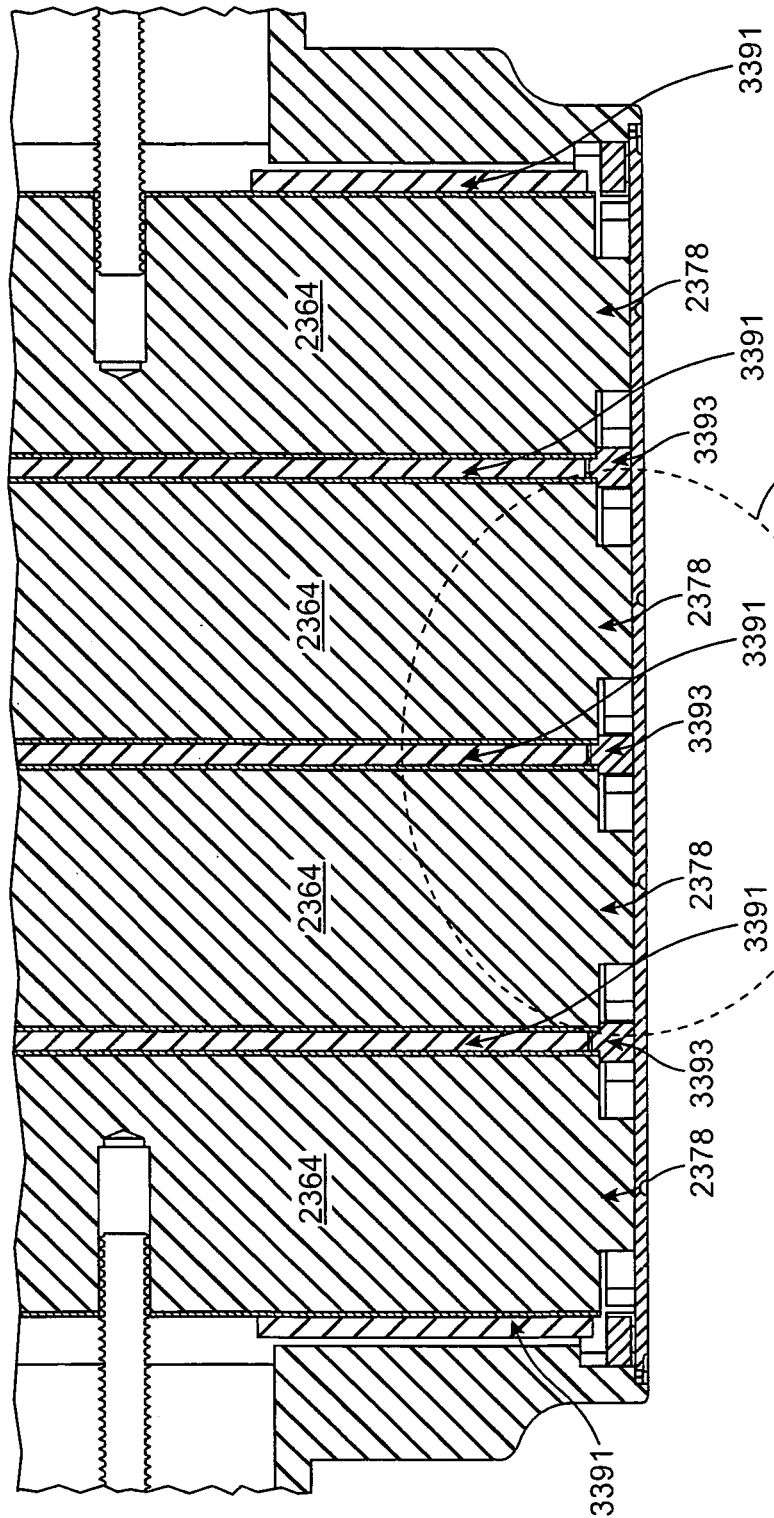
FIG. 18 is a cutaway side view of a portion antenna array according to an embodiment of the invention.
Figure 19:
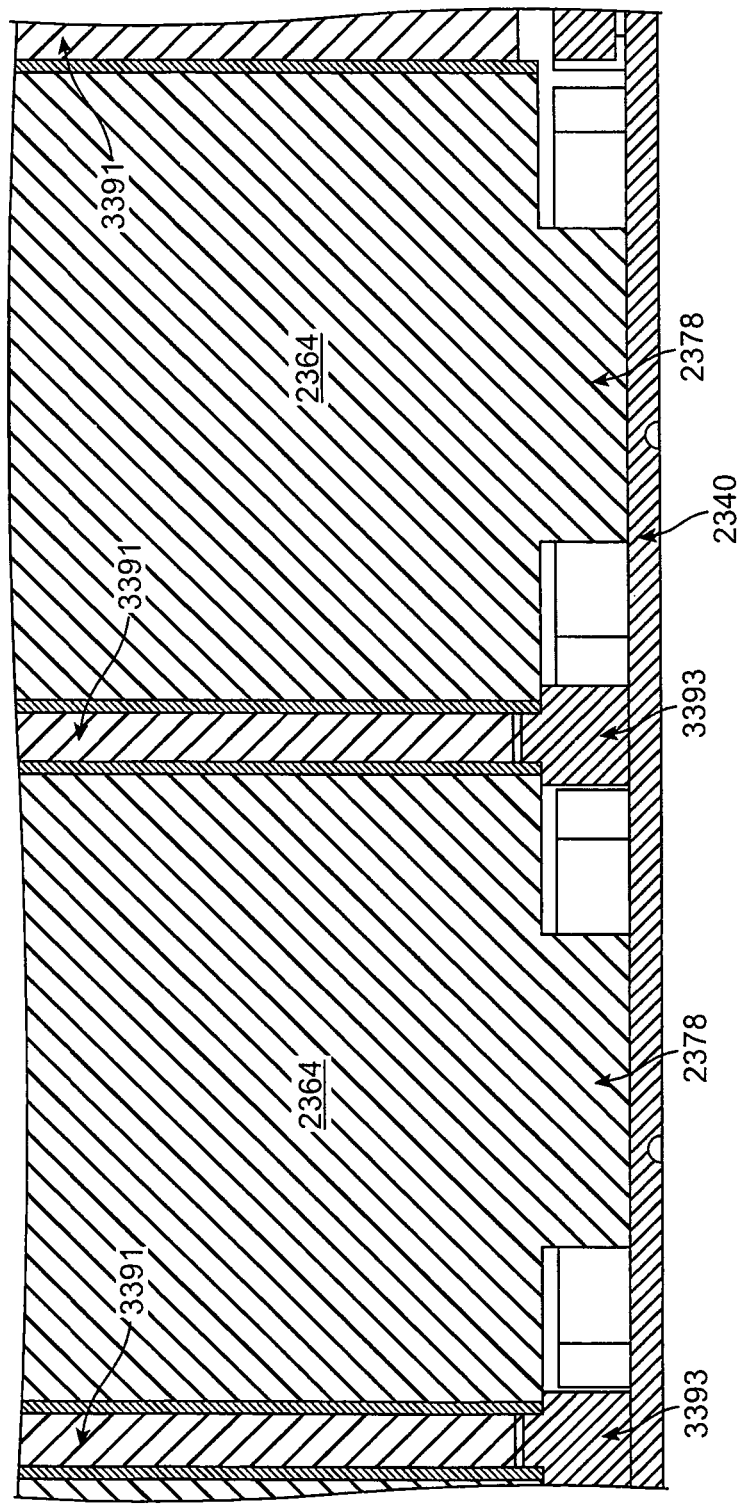
FIG. 19 is a cutaway side view of a portion antenna array according to an embodiment of the invention.

FIG. 17 is an end view of a portion of antenna array 2355 according to an embodiment of the invention. FIG. 18 is a cutaway side view of a portion antenna array 2355 according to an embodiment of the invention. FIG. 19 is a cutaway side view of a portion antenna array 2355 according to an embodiment of the invention. According to an embodiment of the invention antenna array 2355 includes coolant chambers 2360 (for example coolant chambers 2360a, 2360b, 2360c and 2360d), intermediate scattering elements 3393, separation ribs 2393 and scattering elements 2378 (for example scattering elements 2378a, 2378b, 2378c and 2378d). According to an embodiment of the invention scattering elements 2378 may also be referred to as central scattering elements. According to an embodiment of the invention coolant chambers 2360a-2360d may be located beneath waveguide antenna 2364a-2364d. According to an embodiment of the invention coolant chambers 2360 may include separation ribs 2393 on either side of antenna array 2355 and intermediate scattering elements 3393 between antennas 2364. According to an embodiment of the invention an intermediate scattering element 3393 may be positioned between waveguide antenna 2364a and waveguide antenna 2364b. According to an embodiment of the invention an intermediate scattering element 3393 may be positioned between waveguide antenna 2364b and waveguide antenna 2364c. According to an embodiment of the invention an intermediate scattering element 3393 may be positioned between waveguide antenna 2364c and waveguide antenna 2364d. According to an embodiment of the invention cooling fluid flowing through coolant chambers 2360 may have a flow rate of between approximately 200 milliliters per minute and approximately 450 milliliters per minute and preferably approximately 430 milliliters per minute. According to an embodiment of the invention coolant chambers 2360 may be designed to ensure that the flow rate through each coolant chamber 2360 is substantially the same. According to an embodiment of the invention coolant the flow rate of cooling fluid through coolant chamber 2360a is the same as the flow rate of cooling fluid through coolant chamber 2360b. According to an embodiment of the invention coolant the flow rate of cooling fluid through coolant chamber 2360a is the same as the flow rate of cooling fluid through coolant chambers 2360b, 2360c and 2360d. According to an embodiment of the invention cooling fluid flowing through coolant chamber 2360 may have a temperature of between approximately 8 degrees centigrade and approximately 22 degrees centigrade and preferably approximately 15 degrees centigrade. According to an embodiment of the invention coolant chambers 2360 may be positioned between an aperture of waveguide antenna 2364 cooling plate 2340. According to an embodiment of the invention scattering elements 2378 may extend into at least a portion of coolant chambers 2360. According to an embodiment of the invention scattering elements 2378 may extend through coolant chambers 2360. According to an embodiment of the invention scattering elements 2378 and intermediate scattering elements 3393 may extend through coolant chambers 2360 to contact a proximal surface of cooling plate 2340. According to an embodiment of the invention elements of coolant chamber 2360 may be smoothed or rounded to promote laminar fluid flow through coolant chambers 2360. According to an embodiment of the invention elements of coolant chambers 2360 may be smoothed to reduce the generation of air bubbles in coolant chamber 2360. According to an embodiment of the invention scattering elements 2378 which extend into coolant chambers 2360 may be rounded to promote laminar flow and prevent the buildup of bubbles in coolant chamber 2360. According to an embodiment of the invention scattering elements 2378 may be formed in the shape of ovals or racetracks. According to an embodiment of the invention square edges or sharp corners in coolant chamber 2360 may result in undesirable flow characteristics, including the generation of air bubbles, as cooling fluid moves through coolant chamber 2360. According to an embodiment of the invention intermediate scattering elements 3393 may be positioned between separate individual coolant chambers 2360. According to an embodiment of the invention intermediate scattering elements 3393 may be positioned such that they facilitate equalized cooling across cooling plate 2340. According to an embodiment of the invention intermediate scattering elements 3393 may be sized such that they have a width which is equal to or less than the separation distance between apertures of waveguide antennas 2364. According to an embodiment of the invention intermediate scattering elements 3393 may be sized and positioned such that they are not positioned an aperture of waveguide antenna 2364. According to an embodiment of the invention intermediate scattering elements 3393 may be sized and positioned such that they modify a microwave field as it travels through coolant chamber 2360. According to an embodiment of the invention intermediate scattering elements 3393 may be sized and positioned such that they modify a microwave field radiated from waveguide antenna 2364. According to an embodiment of the invention intermediate scattering elements 3393 may be sized and positioned such that they spread out a microwave field as it travels through coolant chamber 2360. According to an embodiment of the invention intermediate scattering elements 3393 may cause disruption or perturbation of microwave energy radiated from waveguide antenna 2364. According to an embodiment of the invention intermediate scattering elements 3393 may be made of materials which will not rust or degrade in cooling fluid. According to an embodiment of the invention intermediate scattering elements 3393 may be made of materials which improve the SAR pattern in tissue. According to an embodiment of the invention intermediate scattering elements 3393 may be made of materials, such as dielectric materials, which are used to form scattering elements 2378. According to an embodiment of the invention FIGS. 17 through 19 may also include waveguide assembly 2358, feed connectors 2388, antenna chamber 2377, spacers 3391, cradle channels 2389 and antenna cradle 2374.

According to an embodiment of the invention intermediate scattering elements 3393 may be positioned between waveguide antennas 2364. According to an embodiment of the invention the size and shape of the intermediate scattering elements 3393 may be designed to optimize the size and shape of lesions developed in the skin between waveguide antennas 2364. According to an embodiment of the invention intermediate scattering elements 3393 may make lesions created in tissue between waveguide antennas 2364 larger and more spread out. According to an embodiment of the invention intermediate scattering elements 3393 may make lesions created in tissue between waveguide antennas 2364 narrower. According to an embodiment of the invention intermediate scattering elements 3393 may have an optimal length which is shorter than the length of scattering elements 2378. According to an embodiment of the invention scattering elements 2378 may be approximately 7 millimeters in length. According to an embodiment of the invention intermediate scattering elements 3393 may have an optimal length which is approximately 6.8 millimeters. According to an embodiment of the invention intermediate scattering elements 3393 may be manufactured from, for example, alumina. According to an embodiment of the invention intermediate scattering elements 3393 may be manufactured from, for example, a material which is approximately 96% alumina. According to an embodiment of the invention intermediate scattering elements 3393 may be manufactured from, for example, silicone. According to an embodiment of the invention the intermediate scattering elements 3393 may be manufactured from a material having the same dielectric constant as scattering elements 2378. According to an embodiment of the invention the intermediate scattering elements 3393 may be manufactured from a material having approximately the same dielectric constant as scattering elements 2378. According to an embodiment of the invention intermediate scattering elements 3393 may be manufactured from a material having a dielectric constant of approximately 10. According to an embodiment of the invention intermediate scattering elements 3393 may be manufactured from a material having a dielectric constant of approximately 3. According to an embodiment of the invention increasing the dielectric constant of intermediate scattering element 3393 may reduce the size of a lesion created in skin between waveguide antennas 2364. According to an embodiment of the invention intermediate scattering elements 3393 may be inserted into tung and grove slots between wave antennas 2364. According to an embodiment of the invention thermocouples may be positioned beneath one or more of intermediate scattering elements 3393. According to an embodiment of the invention thermocouples may be positioned each of intermediate scattering elements 3393.

Figure 20:
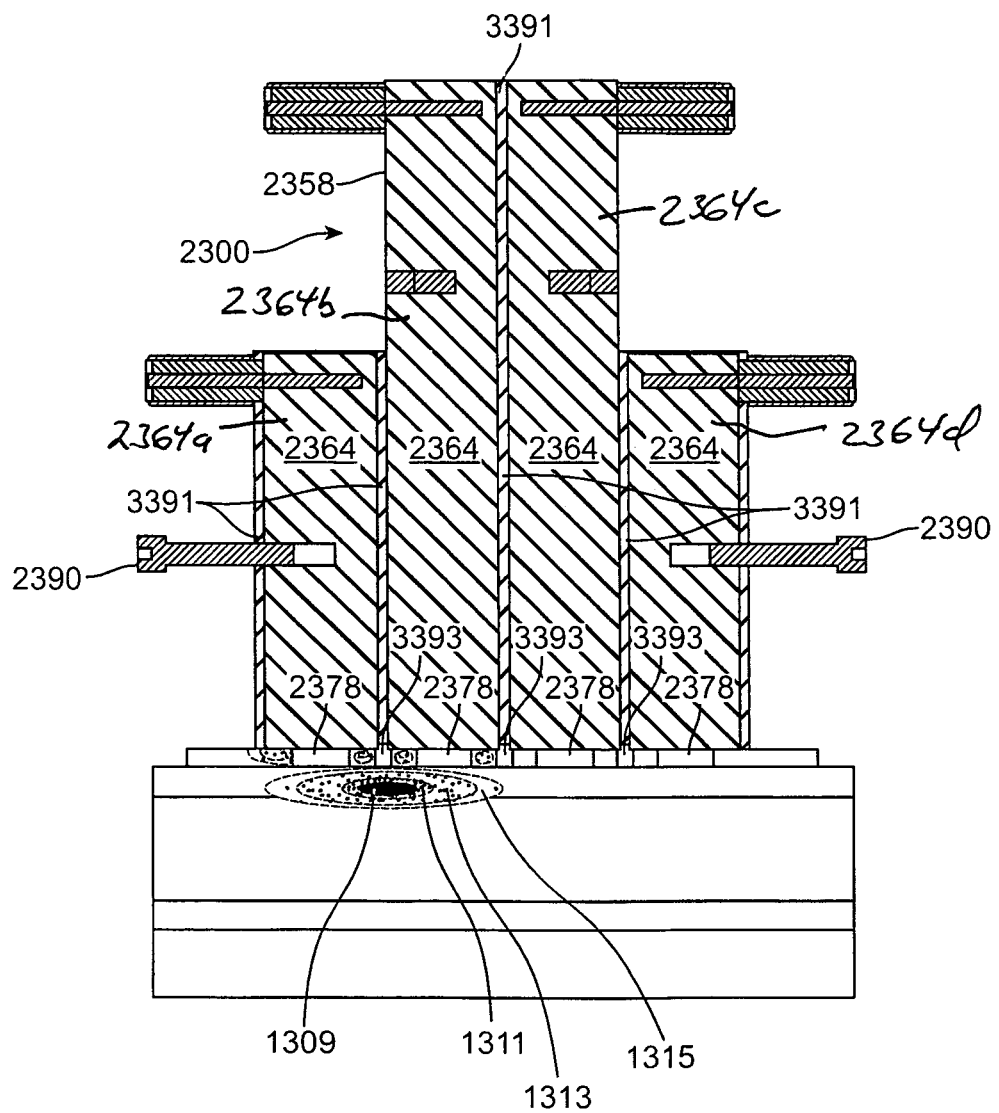
FIG. 20 is a simplified cutaway view of a medical treatment device with tissue engaged according to an embodiment of the invention.
Figure 21:
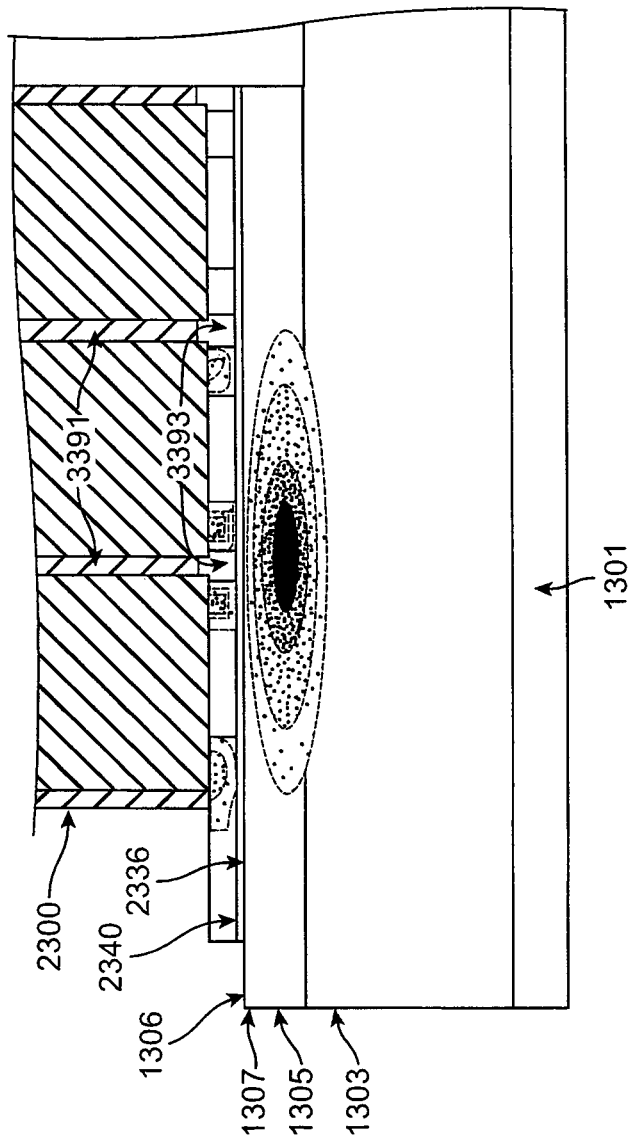
FIG. 21 is a simplified cutaway view of a medical treatment device with tissue engaged according to an embodiment of the invention.
Figure 22:
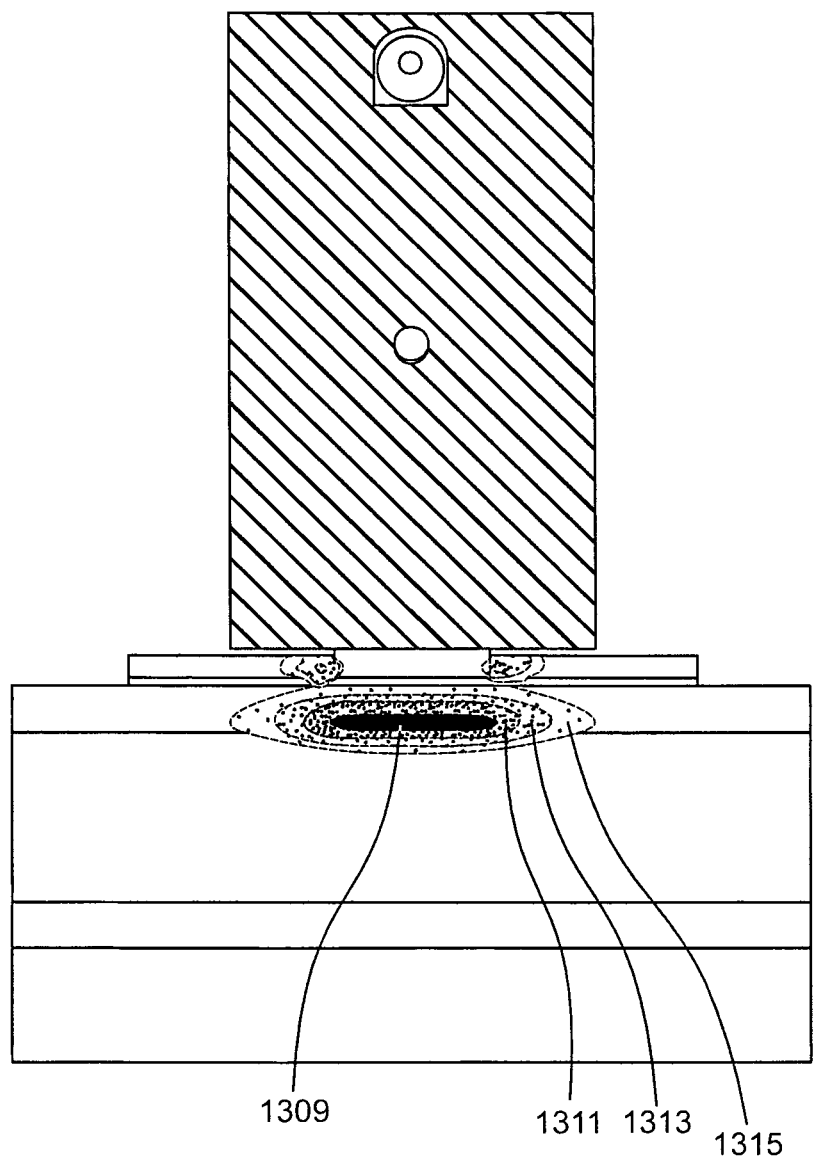
FIG. 22 is a simplified cutaway view of a medical treatment device with tissue engaged according to an embodiment of the invention.

FIGS. 20, 21 and 22 are simplified cutaway views of a medical treatment device 2300 with tissue engaged according to an embodiment of the invention. According to an embodiment of the invention skin 1307 is engaged in treatment device 2300. According to an embodiment of the invention dermis 1305 and hypodermis 1303 are engaged in medical treatment device 2300. According to an embodiment of the invention skin surface 1306 is engaged in medical treatment device 2300 such that skin surface 1306 is in thermal contact with at least a portion of cooling plate 2340. According to an embodiment of the invention skin surface 1306 is engaged in medical treatment device 2300 such that skin surface 1306 is in contact with at least a portion of tissue interface 2336. According to an embodiment of the invention a vacuum pressure may be used to elevate dermis 1305 and hypodermis 1303, separating dermis 1305 and hypodermis 1303 from muscle 1301. According to an embodiment of the invention vacuum pressure may be used to elevate dermis 1305 and hypodermis 1303, separating dermis 1305 and hypodermis 1303 from muscle 1301 to, for example, protect muscle 1301 by limiting or eliminating the electromagnetic energy which reaches muscle 1301. According to an embodiment of the invention waveguide assembly 2358 may include one or more waveguide antennas 2364. According to an embodiment of the invention electromagnetic energy, such as, for example, microwave energy may be radiated into dermis 1305 by medical treatment device 2300. According to an embodiment of the invention medical treatment device 2300 may include coolant chamber 2360 and cooling plate 2340. According to an embodiment of the invention a peak which may be, for example, a peak SAR, peak power loss density or peak temperature, is generated in first tissue region 1309. According to an embodiment of the invention first tissue region 1309 may represent a lesion created by energy, such as, for example, microwave energy radiated from medical treatment device 2300. According to an embodiment of the invention first tissue region 1309 may represent a lesion created by microwave energy radiated from one or more of waveguide antennas 2364. According to an embodiment of the invention first tissue region 1309 may be initiated in skin 1307 between first waveguide antenna 2364 and a second waveguide antenna 2364. According to an embodiment of the invention first tissue region 1309 may be initiated in skin 1307 between first waveguide antenna 2364a and a second waveguide antenna 2364b. According to an embodiment of the invention first tissue region 1309 may be initiated in skin 1307 underlying intermediate scattering element 3393. According to an embodiment of the invention a reduced magnitude which may be, for example, a reduced SAR, reduced power loss density or reduced temperature, is generated in second tissue region 1311 with further reduced magnitudes in third tissue region 1313 and fourth tissue region 1315. As illustrated in FIGS. 20 through 22, dermis 1305 is separated from hypodermis 1303 by interface 1308. As illustrated in FIGS. 20 through 22 interface 1308 may be idealized as a substantially straight line for the purposes of simplified illustration however in actual tissue, interface 1308 may be a non-linear, non continuous, rough interface which may also include many tissue structures and groups of tissue structures which cross and interrupt tissue interface 1308. According to an embodiment of the invention electromagnetic radiation may be radiated at a frequency of, for example, between 5 and 6.5 GHz. According to an embodiment of the invention electromagnetic radiation may be radiated at a frequency of, for example, approximately 5.8 GHz. According to an embodiment of the invention scattering element 2378 may be located in coolant chamber 2360 and intermediate scattering elements 3393 may be located between coolant chambers 2360. According to an embodiment of the invention scattering element 2378 and intermediate scattering elements 3393 may be used to, for example, spread and flatten first tissue region 1309. According to an embodiment of the invention scattering element 2378 and intermediate scattering elements 3393 may be used to, for example, spread and flatten a region, such as first tissue region 1309, of peak SAR in tissue. According to an embodiment of the invention scattering element 2378 and intermediate scattering elements 3393 may be used to, for example, spread and flatten a region, such as first tissue region 1309, of peak power loss density in tissue. According to an embodiment of the invention scattering element 2378 and intermediate scattering elements 3393 may be used to, for example, spread and flatten a region, such as first tissue region 1309, of peak temperature in tissue. According to an embodiment of the invention scattering element 2378 and scattering elements 3393 may be used to, for example, spread and flatten lesions formed in first tissue region 1309. According to an embodiment of the invention the creation of lesions, such as for example, a lesion in tissue region 1309 may be used to treat the skin of patients. According to an embodiment of the invention the creation of lesions, such as for example, a lesion in tissue region 1309 may be used to damage or destroy structures, such as, for example, sweat glands in the skin of a patient.

Figure 23:
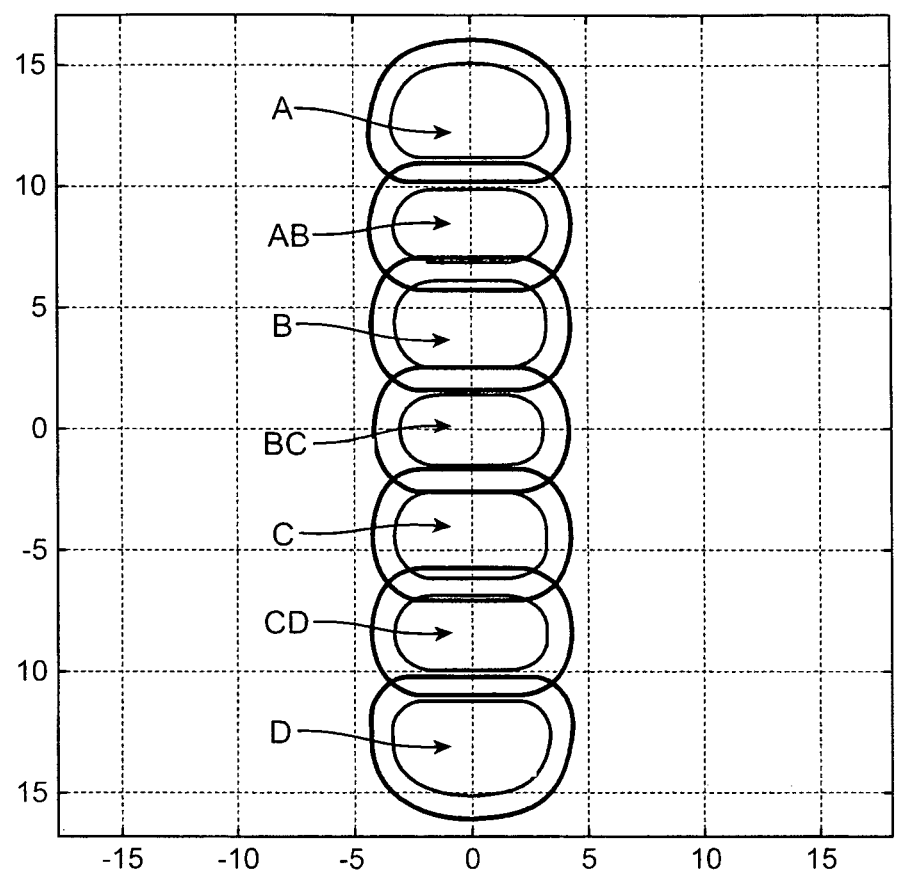
FIG. 23 is a graphical illustration of a pattern of lesions in tissue according to an embodiment of the invention.

FIG. 23 is a graphical illustration of a pattern of lesions in tissue according to an embodiment of the invention. According to an embodiment of the invention lesions may be created in a predetermined order, such as, for example A-B-C-D where: A represents a lesion initiated directly under waveguide antenna 2364a; B represents a lesion initiated directly under waveguide antenna 2364b; C represents a lesion initiated directly under waveguide antenna 2364c; D represents a lesion initiated directly under waveguide antenna 2364d. According to an embodiment of the invention lesions may be created in a predetermined order such as, for example, A-AB-B-BC-C-CD-D where: A represents a lesion initiated directly under waveguide antenna 2364a; AB represents a lesion initiated under the intersection between waveguide antenna 2364a and waveguide antenna 2364b; B represents a lesion initiated directly under waveguide antenna 2364b; BC represents a lesion initiated under the intersection between waveguide antenna 2364b and waveguide antenna 2364c; C represents a lesion initiated directly under waveguide antenna 2364c; CD represents a lesion initiated under the intersection between waveguide antenna 2364c and waveguide antenna 2364d; and D represents a lesion initiated directly under waveguide antenna 2364d. According to an embodiment of the invention a lesion AB may be created between waveguide antenna 2364a and waveguide antenna 2364b, by driving waveguide antenna 2364a and waveguide antenna 2364b simultaneously in phase and with a balanced output from each antenna. According to an embodiment of the invention a lesion BC may be created between waveguide antenna 2364b and waveguide antenna 2364c, by driving waveguide antenna 2364b and waveguide antenna 2364c simultaneously in phase and with a balanced output from each waveguide antenna.

According to an embodiment of the invention a lesion CD may be created between waveguide antenna 2364c and waveguide antenna 2364d, by driving waveguide antenna 2364c and waveguide antenna 2364d simultaneously in phase and with a balanced output from each waveguide antenna.

Figure 24:
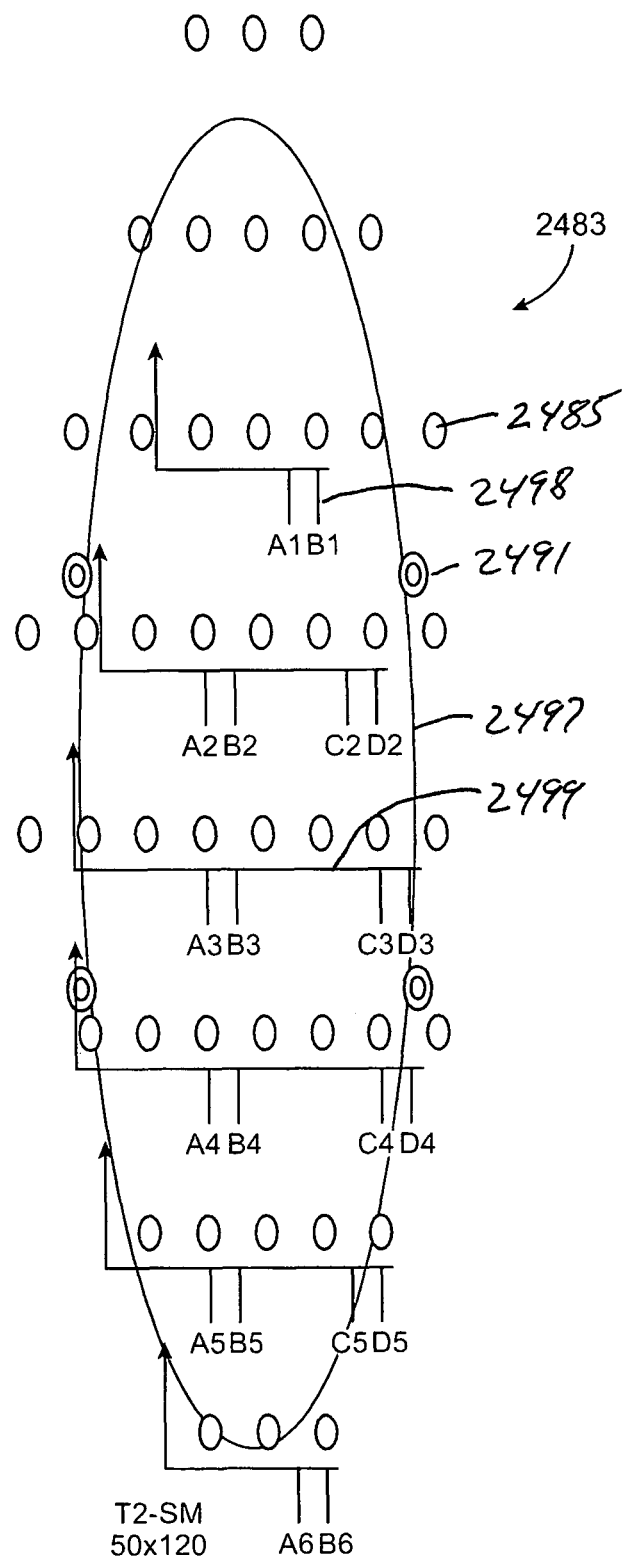
FIG. 24 illustrates a treatment template according to an embodiment of the invention.

FIG. 24 is a treatment template 2483 according to an embodiment of the invention. According to an embodiment of the invention treatment template 2483 may include axilla outline 2497, anesthesia injection sites 2485, landmark alignment marks 2497, device alignment points 2498 and device alignment lines 2499. According to an embodiment of the invention axilla outline 2497 may be matched to the hair bearing area of a patient to select an appropriate treatment template 2483. According to an embodiment of the invention anesthesia injection sites 2485 may be used to identify appropriate points in the axilla for the injection of anesthesia. According to an embodiment of the invention landmark alignment marks may be used to align treatment template 2483 to landmarks, such as, for example, tattoos or moles on the axilla. According to an embodiment of the invention device alignment points 2498 may be used in conjunction with alignment features 3352 to properly align medical treatment device 2300. According to an embodiment of the invention device alignment lines 2499 may be used in conjunction with an outer edge of compliant member 2375 to properly align medical treatment device 2300. According to an embodiment of the invention treatment template 2384 provides guidance and placement information for medical treatment device 2300 in matrix format.

According to an embodiment of the invention A medical device disposable may include: a tissue chamber may have a tissue opening at a distal end and a rigid surface surrounding the tissue opening; an applicator chamber; a flexible bio-barrier at a proximal end of the tissue chamber the flexible bio-barrier separating the tissue chamber and the applicator chamber, a portion of the flexible bio-barrier forming a tissue contacting surface; a compliant member surrounding the tissue opening, the compliant member may have a proximal opening adjacent the tissue opening and a distal opening, wherein the distal opening may be larger than the proximal opening.

According to an embodiment of the invention the medical device disposable compliant member may be positioned at an angle of approximately fifty-three degrees with respect to the rigid surface. According to an embodiment of the invention the compliant member may include a wall connecting the proximal opening and the distal opening and the wall may be angled approximately fifty-three degrees with respect to the rigid surface. According to an embodiment of the invention the compliant member may further include an outer rim positioned around the distal opening. According to an embodiment of the invention: the outer rim may extend a distance of approximately 0.033 inches from the distal opening; the compliant member may have a height of approximately 0.25 inches; the tissue opening may have a long axis and a short axis, the tissue opening long axis may be approximately 1.875 inches and the tissue opening short axis may be approximately 1.055 inches; the distal opening in the compliant member may have a long axis and a short axis, the distal opening long axis may be approximately 2.429 inches and the distal opening short axis may be approximately 1.609 inches; the tissue contact surface may have a long axis and a short axis, the long axis may be approximately 1.54 inches and the short axis may be approximately 0.700 inches. According to an embodiment of the invention the wall may be substantially straight. According to an embodiment of the invention the compliant member may include one or more alignment marks, at least one of the alignment marks may be positioned on a long side of the compliant member. According to an embodiment of the invention the alignment marks may be positioned on a wall of the skirt and may extend from approximately the rim toward the tissue opening. According to an embodiment of the invention the alignment marks may move with respect to an applicator positioned in the applicator chamber when the medical device disposable is pressed against tissue with sufficient pressure to compress the compliant member. According to an embodiment of the invention the wall may have a thickness of approximately 0.050 inches. According to an embodiment of the invention the tissue chamber may include a chamber wall extending from the tissue opening to approximately the tissue contact surface, the wall may also include a substantially smooth, radiused surface. According to an embodiment of the invention the radiused surface may have a radius of approximately three-sixteenths of an inch. According to an embodiment of the invention the compliant member may have durometer density rating of approximately A60.

According to an embodiment of the invention A medical device disposable may include: a tissue chamber including a tissue contact surface at a proximal end of the tissue chamber and a tissue opening at a distal end of the tissue chamber; an applicator chamber; a flexible bio-barrier at a proximal end of the tissue chamber the flexible bio-barrier separating the tissue chamber and the applicator chamber, the flexible bio-barrier forming at least a portion of the tissue contact surface; a vacuum port; a vacuum circuit connecting the tissue chamber, the applicator chamber and the vacuum port, the vacuum circuit including a vacuum passage.

According to an embodiment of the invention the vacuum circuit may include: a vacuum passage positioned around the tissue contact surface; a vacuum channel positioned around the vacuum passage, the vacuum channel positioned between the vacuum passage and the vacuum port; an applicator bio-barrier positioned between the vacuum port and the applicator chamber, the applicator bio-barrier being substantially permeable to air and substantially impermeable to fluids. According to an embodiment of the invention the vacuum passage may completely surround the tissue interface surface. According to an embodiment of the invention the vacuum passage may substantially surrounds the tissue interface surface. According to an embodiment of the invention the vacuum passage may be positioned in a wall of the tissue chamber adjacent the tissue contact surface. According to an embodiment of the invention vacuum port may be connected to a vacuum tube. According to an embodiment of the invention the vacuum tube may include a generator bio-barrier. According to an embodiment of the invention the generator bio-barrier may be substantially permeable to air and being substantially impermeable to fluids. According to an embodiment of the invention the vacuum channel may include a well region adapted to collect fluids from the tissue chamber. According to an embodiment of the invention a compliant member may surround the tissue opening, the compliant member may have a proximal opening adjacent the tissue opening and a distal opening, wherein the distal opening may be larger than the proximal opening. According to an embodiment of the invention the vacuum passage may be an opening between a wall of the tissue chamber and the tissue bio-barrier. According to an embodiment of the invention the vacuum passage may be approximately 0.020" inches wide. According to an embodiment of the invention the vacuum passage may be greater than approximately 0.010" inches when the medical device disposable may be attached to an applicator. According to an embodiment of the invention the tissue surface may have an area greater than an outer area of an antenna array in an applicator affixed to the medical device disposable. According to an embodiment of the invention the tissue surface may have an area greater than an aperture area of an antenna array in an applicator affixed to the medical device disposable.

According to an embodiment of the invention a method of creating a lesion in skin is described, the method including the steps of: positioning an apparatus including a plurality of antennas adjacent a skin surface; supplying energy to a first antenna at a first power level for a first time period; supplying energy to a second antenna at a second power level for a second time period; supplying energy simultaneously to both the first antenna and the second antenna for a third time period, wherein, during the third time period the energy may be supplied to the first antenna at a third power level and the energy may be supplied to the second antenna at a fourth power level. According to an embodiment of the invention the energy supplied to the first antenna may be in phase with the energy supplied to the second antenna. According to an embodiment of the invention the energy supplied to the first antenna may be phase shifted from the energy supplied to the second antenna. According to an embodiment of the invention the energy supplied to the first antenna may be phase shifted approximately one hundred eighty degrees from the energy supplied to the second antenna. According to an embodiment of the invention the energy supplied to the first antenna may be phase shifted between one and one hundred eighty degrees from the energy supplied to the second antenna. According to an embodiment of the invention the energy output from the first antenna may be substantially in phase with energy output from the second antenna. According to an embodiment of the invention the energy supplied to the first antenna may be phase shifted from the energy supplied to the second antenna, the phase shift being sufficient to cause energy output from the first antenna to be in phase with energy output from the second antenna. According to an embodiment of the invention the energy supplied to the first and second antennas may be microwave energy having a frequency of approximately 5.8 GHz. According to an embodiment of the invention the first and second antennas may be microwave antennas. According to an embodiment of the invention the first and second antennas may be waveguide antennas. According to an embodiment of the invention the first and the second power levels may be substantially equal. According to an embodiment of the invention the first power level may be greater than the second power level. According to an embodiment of the invention the power emitted by the first antenna may be substantially equal to power emitted by the second antenna.

According to an embodiment of the invention a medical device applicator may include: an antenna array including at least two antenna apertures; at least one intermediate scattering element positioned outside the apertures wherein the at least one intermediate scattering element may be further positioned between the apertures. According to an embodiment of the invention each of the apertures may be substantially rectangular in shape, the apertures including a long axis and a short axis. According to an embodiment of the invention each of the intermediate scattering elements may include a long axis and a short axis wherein the long axis of the at least one intermediate scattering element may be substantially parallel to the long axis of the aperture. According to an embodiment of the invention the medical device applicator may include a cooling plate and the intermediate scattering element may be positioned between the antenna apertures and the cooling plate. According to an embodiment of the invention the medical device applicator may further include one or more coolant chambers positioned between the cooling plate and the antenna aperture. According to an embodiment of the invention the medical device applicator may include at least two central scattering elements positioned under the aperture wherein the at least one intermediate scattering element may be positioned between the central scattering elements. According to an embodiment of the invention the central scattering elements may be positioned substantially in a center of one of the antenna apertures. According to an embodiment of the invention the long axis of the intermediate scattering element may be shorter than the longest dimension of the central scattering element. According to an embodiment of the invention the intermediate scattering element may be manufactured from a material which may have the same dielectric constant as the central scattering element. According to an embodiment of the invention the intermediate scattering element may be made from alumina. According to an embodiment of the invention the intermediate scattering element may be made from a material which may be more than 90 percent alumina. According to an embodiment of the invention the intermediate scattering element may be made from a material which may be approximately 96 percent alumina. According to an embodiment of the invention the intermediate scattering element may be made from, for example silicone. According to an embodiment of the invention one or more temperature measurement devices may be positioned on the cooling plate under the intermediate scattering element. According to an embodiment of the invention the one or more temperature measurement device may be one or more thermocouples.

According to an embodiment of the invention a medical device applicator may include at least a first and a second waveguide antenna and at least a first electrically conductive shim positioned between the waveguide antennas. According to an embodiment of the invention each of the waveguide antennas may include: a dielectric core having four sides; metal plating on three sides of the dielectric core, the fourth side of the dielectric core forming an antenna aperture. According to an embodiment of the invention the electrically conductive shim may be copper. According to an embodiment of the invention the electrically conductive shim may be approximately 0.025 inches thick. According to an embodiment of the invention the electrically conductive shim may be positioned between the first and second waveguide antennas such that an edge of the electrically conductive shim may be adjacent the antenna apertures. According to an embodiment of the invention an intermediate scattering element may be positioned under the conductive shim. According to an embodiment of the invention central scattering elements may be positioned under the antenna apertures. According to an embodiment of the invention the medical device applicator may include a cooling plate. According to an embodiment of the invention the intermediate scattering element and the central scattering element may be positioned between the antenna apertures and the cooling plate. According to an embodiment of the invention the medical device applicator may include a coolant chamber positioned between the antenna apertures and the cooling plate. According to an embodiment of the invention the medical device applicator may include temperature sensors positioned on the cooling plate.

We claim:

1. A method of creating a lesion in skin, said method comprising the steps of:
    positioning an apparatus including a plurality of waveguide antennas adjacent a skin surface with an output of the waveguide antennas being separated from the skin surface by a cooling chamber and a cooling plate;
    supplying energy to a first waveguide antenna at a first power level for a first predetermined time period;
    supplying energy to a second waveguide antenna at a second power level for a second predetermined time period;
    supplying energy simultaneously to both said first waveguide antenna and said second waveguide antenna for a third time period, wherein, during said third time period said energy is supplied to said first waveguide antenna at a third power level and said energy is supplied to said second waveguide antenna at a fourth power level, such that the first waveguide antenna and the second waveguide antenna have a balanced output.

2. The method of claim 1 wherein said energy supplied to said first waveguide antenna is in phase with said energy supplied to said second waveguide antenna.

3. The method of claim 1 wherein said energy supplied to said first waveguide antenna is phase shifted from said energy applied to said second waveguide antenna.

4. The method of claim 3 wherein said energy supplied to said first waveguide antenna is phase shifted 180 degrees from said energy applied to said second waveguide antenna.

5. The method of claim 3 wherein said energy supplied to said first waveguide antenna is phase shifted between 1-180 degrees from said energy applied to said second waveguide antenna.

6. The method of claim 5 wherein energy output from said first waveguide antenna is in phase with energy output from said second waveguide antenna.

7. The method of claim 3 wherein said energy supplied to said first waveguide antenna is phase shifted from said energy applied to said second waveguide antenna, said phase shift being sufficient to cause energy output from said first waveguide antenna to be in phase with energy output from said second waveguide antenna.

8. The method of claim 7 wherein said first power level is greater than said second power level.

9. The method of claim 8 wherein energy output from said first waveguide antenna is equal to energy output from said second waveguide antenna.

10. The method of claim 1 wherein said first and second power levels are equal.

* * * * *